United States Patent
Kugler et al.

(10) Patent No.: US 8,202,246 B2
(45) Date of Patent: Jun. 19, 2012

(54) CROSSING OCCLUSIONS IN BLOOD VESSELS

(75) Inventors: Chad John Kugler, Buffalo, MN (US); Matthew Jonathan Olson, Crystal, MN (US); Ross Arlen Olson, Anoka, MN (US); David B. Robinson, Chanhassen, MN (US); Peter Alan Jacobs, Minneapolis, MN (US)

(73) Assignee: BridgePoint Medical, Inc., Plymouth, MN (US)

( * ) Notice: Subject to any disclaimer, the term of this patent is extended or adjusted under 35 U.S.C. 154(b) by 471 days.

(21) Appl. No.: 12/320,792

(22) Filed: Feb. 4, 2009

(65) Prior Publication Data

US 2009/0209910 A1 Aug. 20, 2009

Related U.S. Application Data

(60) Provisional application No. 61/063,756, filed on Feb. 5, 2008.

(51) Int. Cl.
*A61M 31/00* (2006.01)
*A61M 37/00* (2006.01)

(52) U.S. Cl. .................................................. 604/103.1

(58) Field of Classification Search ............... 600/585; 604/164.01, 164.11, 264, 272, 523, 158–161, 604/103.1; 606/108
See application file for complete search history.

(56) References Cited

U.S. PATENT DOCUMENTS

| | | | |
|---|---|---|---|
| 3,749,086 A | 7/1973 | Kline et al. | |
| 4,020,829 A | 5/1977 | Wilson et al. | |
| 4,080,706 A | 3/1978 | Heilman et al. | |
| 4,233,983 A | 11/1980 | Rocco | |
| 4,534,363 A | 8/1985 | Gold | |
| 4,545,390 A | 10/1985 | Leary | |
| 4,569,347 A | 2/1986 | Frisbie | |
| 4,581,017 A | 4/1986 | Sahota | |
| 4,619,274 A | 10/1986 | Morrison | |
| 4,621,636 A | 11/1986 | Fogarty | |
| 4,676,249 A | 6/1987 | Arenas et al. | |
| 4,721,117 A | 1/1988 | Mar et al. | |

(Continued)

FOREIGN PATENT DOCUMENTS

CA 2 209 637 7/1996

(Continued)

OTHER PUBLICATIONS

International Preliminary Report on Patentability for PCT/US2009/033076 issued on Feb. 5, 2008 (10 pages).

(Continued)

*Primary Examiner* — Christopher D Koharski
(74) *Attorney, Agent, or Firm* — Finnegan, Henderson, Farabow, Garrett & Dunner, LLP

(57) ABSTRACT

The present disclosure is directed a method of facilitating treatment via a vascular wall defining a vascular lumen containing an occlusion therein. The method may include providing a first intravascular device having a distal portion and at least one aperture and positioning the distal portion of the first intravascular device in the vascular wall. The method may further include providing a reentry device having a body and a distal tip, the distal tip having a natural state and a compressed state and inserting the distal tip, in the compressed state, in the distal portion of the first intravascular device. The method may further include advancing the distal tip, in the natural state, through the at least one aperture of the first intravascular device.

53 Claims, 31 Drawing Sheets

U.S. PATENT DOCUMENTS

| | | |
|---|---|---|
| 4,747,821 A | 5/1988 | Kensey et al. |
| 4,748,986 A | 6/1988 | Morrison et al. |
| 4,762,130 A | 8/1988 | Fogarty et al. |
| 4,763,647 A | 8/1988 | Gambale |
| 4,774,949 A | 10/1988 | Fogarty |
| 4,819,634 A | 4/1989 | Shiber |
| 4,832,047 A | 5/1989 | Sepetka et al. |
| 4,841,976 A | 6/1989 | Packard et al. |
| 4,878,495 A | 11/1989 | Grayzel |
| 4,925,445 A | 5/1990 | Sakamoto et al. |
| 4,932,419 A | 6/1990 | de Toledo |
| 4,976,689 A | 12/1990 | Buchbinder et al. |
| 4,979,939 A | 12/1990 | Shiber |
| 4,984,581 A | 1/1991 | Stice |
| 4,990,134 A | 2/1991 | Auth |
| 4,991,602 A | 2/1991 | Amplatz et al. |
| 5,052,404 A | 10/1991 | Hodgson |
| 5,067,489 A | 11/1991 | Lind |
| 5,069,226 A | 12/1991 | Yamauchi et al. |
| 5,071,406 A | 12/1991 | Jang |
| 5,118,907 A | 6/1992 | Stout et al. |
| 5,120,308 A | 6/1992 | Hess |
| 5,127,917 A | 7/1992 | Niederhauser et al. |
| 5,129,890 A | 7/1992 | Bates et al. |
| 5,143,122 A | 9/1992 | Adkins |
| 5,147,317 A | 9/1992 | Shank et al. |
| 5,154,705 A | 10/1992 | Fleischhacker et al. |
| 5,171,383 A | 12/1992 | Sagaye et al. |
| 5,174,302 A | 12/1992 | Palmer |
| 5,193,546 A | 3/1993 | Shaknovich |
| 5,201,753 A | 4/1993 | Lampropoulos et al. |
| 5,213,111 A | 5/1993 | Cook et al. |
| 5,228,453 A | 7/1993 | Sepetka |
| 5,230,348 A | 7/1993 | Ishibe et al. |
| 5,238,004 A | 8/1993 | Sahatjian et al. |
| 5,242,759 A | 9/1993 | Hall |
| 5,243,996 A | 9/1993 | Hall |
| 5,259,393 A | 11/1993 | Corso, Jr. et al. |
| 5,263,493 A | 11/1993 | Avitall |
| 5,275,610 A | 1/1994 | Eberbach |
| 5,282,478 A | 2/1994 | Fleischhaker, Jr. et al. |
| 5,303,714 A | 4/1994 | Abele et al. |
| 5,324,263 A | 6/1994 | Kraus et al. |
| 5,333,620 A | 8/1994 | Moutafis et al. |
| 5,354,257 A | 10/1994 | Roubin et al. |
| 5,354,623 A | 10/1994 | Hall |
| 5,356,418 A | 10/1994 | Shturman |
| 5,363,847 A | 11/1994 | Viera |
| 5,365,942 A | 11/1994 | Shank |
| 5,368,048 A | 11/1994 | Stoy et al. |
| 5,368,049 A | 11/1994 | Raman et al. |
| 5,372,144 A | 12/1994 | Mortier et al. |
| 5,372,587 A | 12/1994 | Hammerslag et al. |
| 5,373,856 A | 12/1994 | Grenouillet |
| 5,379,779 A | 1/1995 | Rowland et al. |
| 5,383,856 A | 1/1995 | Bersin |
| 5,385,152 A | 1/1995 | Abele et al. |
| 5,409,453 A | 4/1995 | Lundquist et al. |
| 5,415,178 A | 5/1995 | Hsi et al. |
| 5,415,637 A | 5/1995 | Khosravi |
| 5,421,349 A | 6/1995 | Rodriguez et al. |
| 5,443,907 A | 8/1995 | Slaikeu et al. |
| 5,458,585 A | 10/1995 | Salmon et al. |
| 5,464,395 A | 11/1995 | Faxon et al. |
| 5,477,864 A | 12/1995 | Davidson |
| 5,488,959 A | 2/1996 | Ales |
| 5,498,250 A | 3/1996 | Prather |
| 5,501,667 A | 3/1996 | Verduin, Jr. |
| 5,505,702 A | 4/1996 | Arney |
| 5,531,781 A | 7/1996 | Alferness et al. |
| 5,534,007 A | 7/1996 | St Germain et al. |
| 5,542,434 A | 8/1996 | Imran et al. |
| 5,555,883 A | 9/1996 | Avitall |
| 5,571,122 A | 11/1996 | Kelly et al. |
| 5,571,169 A | 11/1996 | Plaia et al. |
| 5,603,720 A | 2/1997 | Kieturakis |
| 5,622,184 A | 4/1997 | Ashby et al. |
| 5,636,641 A | 6/1997 | Fariabi |
| 5,637,089 A | 6/1997 | Abrams et al. |
| 5,640,970 A | 6/1997 | Arenas |
| 5,643,298 A | 7/1997 | Nordgren et al. |
| 5,645,529 A | 7/1997 | Fagan et al. |
| 5,655,548 A | 8/1997 | Nelson et al. |
| 5,664,580 A | 9/1997 | Erickson et al. |
| 5,695,111 A | 12/1997 | Nanis et al. |
| 5,695,506 A | 12/1997 | Pike et al. |
| 5,720,300 A | 2/1998 | Fagan et al. |
| 5,722,424 A | 3/1998 | Engelson |
| 5,728,133 A | 3/1998 | Kontos |
| 5,741,270 A | 4/1998 | Hansen et al. |
| 5,741,429 A | 4/1998 | Donadio, III et al. |
| 5,769,796 A | 6/1998 | Palermo et al. |
| 5,779,721 A | 7/1998 | Nash |
| 5,807,241 A | 9/1998 | Heimberger |
| 5,824,071 A | 10/1998 | Nelson et al. |
| 5,830,222 A | 11/1998 | Makower |
| 5,830,224 A | 11/1998 | Cohn et al. |
| 5,833,631 A | 11/1998 | Nguyen |
| 5,840,046 A | 11/1998 | Deem |
| 5,843,050 A | 12/1998 | Jones et al. |
| 5,871,528 A | 2/1999 | Camps et al. |
| 5,885,227 A | 3/1999 | Finlayson |
| 5,891,055 A | 4/1999 | Sauter |
| 5,910,133 A | 6/1999 | Gould et al. |
| 5,916,194 A | 6/1999 | Jacobsen et al. |
| 5,924,998 A | 7/1999 | Cornelius et al. |
| 5,935,108 A | 8/1999 | Katoh et al. |
| 5,944,686 A | 8/1999 | Patterson et al. |
| 5,947,940 A | 9/1999 | Beisel |
| 5,951,494 A | 9/1999 | Wang et al. |
| 5,954,713 A | 9/1999 | Newman et al. |
| 5,957,900 A | 9/1999 | Ouchi |
| 5,968,064 A | 10/1999 | Selmon et al. |
| 5,984,878 A | 11/1999 | Engelson |
| 5,989,276 A | 11/1999 | Houser et al. |
| 5,997,517 A | 12/1999 | Whitbourne |
| 6,010,449 A | 1/2000 | Selmon et al. |
| 6,013,055 A | 1/2000 | Bampos et al. |
| 6,015,405 A | 1/2000 | Schwartz et al. |
| 6,022,343 A | 2/2000 | Johnson et al. |
| 6,027,460 A | 2/2000 | Shturman |
| 6,036,707 A | 3/2000 | Spaulding |
| 6,036,717 A | 3/2000 | Mers Kelly et al. |
| 6,042,876 A | 3/2000 | Deem |
| 6,059,750 A | 5/2000 | Fogarty et al. |
| 6,068,638 A | 5/2000 | Makower |
| 6,071,281 A | 6/2000 | Burnside et al. |
| 6,071,292 A | 6/2000 | Makower et al. |
| 6,081,738 A | 6/2000 | Hinohara et al. |
| 6,099,542 A | 8/2000 | Cohn et al. |
| 6,106,485 A | 8/2000 | McMahon |
| 6,117,064 A | 9/2000 | Apple et al. |
| 6,120,516 A | 9/2000 | Selmon et al. |
| 6,126,649 A | 10/2000 | VanTassel et al. |
| 6,139,540 A | 10/2000 | Rost et al. |
| 6,155,264 A | 12/2000 | Ressemann et al. |
| 6,157,852 A | 12/2000 | Selmon et al. |
| 6,159,225 A | 12/2000 | Makower |
| 6,183,432 B1 | 2/2001 | Milo |
| 6,186,972 B1 | 2/2001 | Nelson et al. |
| 6,190,353 B1 | 2/2001 | Makower et al. |
| 6,203,559 B1 | 3/2001 | Davis et al. |
| 6,217,527 B1 | 4/2001 | Selmon et al. |
| 6,217,549 B1 | 4/2001 | Selmon et al. |
| 6,221,049 B1 | 4/2001 | Selmon et al. |
| 6,231,546 B1 | 5/2001 | Milo et al. |
| 6,231,587 B1 | 5/2001 | Makower |
| 6,235,000 B1 | 5/2001 | Milo et al. |
| 6,241,667 B1 | 6/2001 | Vetter et al. |
| 6,245,030 B1 | 6/2001 | DuBois et al. |
| 6,246,914 B1 | 6/2001 | de la Rama et al. |
| 6,254,588 B1 | 7/2001 | Jones et al. |
| 6,258,052 B1 | 7/2001 | Milo |
| 6,266,550 B1 | 7/2001 | Selmon et al. |
| 6,277,133 B1 | 8/2001 | Kanesaka |
| 6,283,940 B1 | 9/2001 | Mulholland |
| 6,283,951 B1 | 9/2001 | Flaherty et al. |

| Patent No. | Date | Inventor |
|---|---|---|
| 6,283,983 B1 | 9/2001 | Makower et al. |
| 6,287,317 B1 | 9/2001 | Makower et al. |
| 6,302,875 B1 | 10/2001 | Makower et al. |
| 6,330,884 B1 | 12/2001 | Kim |
| 6,337,142 B2 | 1/2002 | Harder et al. |
| 6,358,244 B1 | 3/2002 | Newman et al. |
| 6,375,615 B1 | 4/2002 | Flaherty et al. |
| 6,379,319 B1 | 4/2002 | Garibotto et al. |
| 6,387,119 B2 | 5/2002 | Wolf et al. |
| 6,398,798 B2 | 6/2002 | Selmon et al. |
| 6,416,523 B1 | 7/2002 | Lafontaine |
| 6,428,552 B1 | 8/2002 | Sparks |
| 6,432,127 B1 | 8/2002 | Kim et al. |
| 6,447,539 B1 | 9/2002 | Nelson et al. |
| 6,475,226 B1 | 11/2002 | Belef et al. |
| 6,485,458 B1 | 11/2002 | Takahashi |
| 6,491,660 B2 | 12/2002 | Guo et al. |
| 6,491,707 B2 | 12/2002 | Makower et al. |
| 6,506,178 B1 | 1/2003 | Schubart et al. |
| 6,508,824 B1 | 1/2003 | Flaherty et al. |
| 6,508,825 B1 | 1/2003 | Selmon et al. |
| 6,511,458 B2 * | 1/2003 | Milo et al. .............. 604/164.13 |
| 6,514,217 B1 | 2/2003 | Selmon et al. |
| 6,544,230 B1 | 4/2003 | Flaherty et al. |
| 6,561,998 B1 | 5/2003 | Roth et al. |
| 6,565,583 B1 | 5/2003 | Deaton et al. |
| 6,569,143 B2 | 5/2003 | Alchas et al. |
| 6,569,145 B1 | 5/2003 | Shmulewitz et al. |
| 6,569,150 B2 | 5/2003 | Teague et al. |
| 6,579,311 B1 | 6/2003 | Makower |
| 6,589,164 B1 | 7/2003 | Flaherty |
| 6,599,304 B1 | 7/2003 | Selmon et al. |
| 6,602,241 B2 | 8/2003 | Makower et al. |
| 6,613,081 B2 | 9/2003 | Kim et al. |
| 6,616,675 B1 | 9/2003 | Evard et al. |
| 6,623,448 B2 | 9/2003 | Slater |
| 6,638,247 B1 | 10/2003 | Selmon et al. |
| 6,638,293 B1 | 10/2003 | Makower et al. |
| 6,655,386 B1 | 12/2003 | Makower et al. |
| 6,656,195 B2 | 12/2003 | Peters et al. |
| 6,660,024 B1 | 12/2003 | Flaherty et al. |
| 6,669,709 B1 | 12/2003 | Cohn et al. |
| 6,685,648 B2 | 2/2004 | Flaherty et al. |
| 6,685,716 B1 | 2/2004 | Flaherty et al. |
| 6,694,983 B2 | 2/2004 | Wolf et al. |
| 6,709,444 B1 | 3/2004 | Makower |
| 6,719,725 B2 | 4/2004 | Milo et al. |
| 6,726,677 B1 | 4/2004 | Flaherty et al. |
| 6,746,426 B1 | 6/2004 | Flaherty et al. |
| 6,746,462 B1 | 6/2004 | Selmon et al. |
| 6,746,464 B1 | 6/2004 | Makower |
| 6,786,884 B1 | 9/2004 | DeCant, Jr. et al. |
| 6,800,085 B2 | 10/2004 | Selmon et al. |
| 6,824,550 B1 | 11/2004 | Noriega et al. |
| 6,830,577 B2 | 12/2004 | Nash et al. |
| 6,837,868 B1 | 1/2005 | Fajnztajn |
| 6,860,892 B1 | 3/2005 | Tanaka et al. |
| 6,863,684 B2 | 3/2005 | Kim et al. |
| 6,866,676 B2 | 3/2005 | Kieturakis et al. |
| 6,884,225 B2 | 4/2005 | Kato et al. |
| 6,905,505 B2 | 6/2005 | Nash et al. |
| 6,929,009 B2 | 8/2005 | Makower et al. |
| 6,936,056 B2 | 8/2005 | Nash et al. |
| 6,942,641 B2 | 9/2005 | Seddon |
| 6,949,125 B2 | 9/2005 | Robertson |
| 6,991,617 B2 | 1/2006 | Hektner et al. |
| 7,004,173 B2 | 2/2006 | Sparks et al. |
| 7,056,325 B1 | 6/2006 | Makower et al. |
| 7,059,330 B1 | 6/2006 | Makower et al. |
| 7,083,588 B1 | 8/2006 | Shmulewitz et al. |
| 7,094,230 B2 | 8/2006 | Flaherty et al. |
| 7,105,031 B2 | 9/2006 | Letort |
| 7,134,438 B2 | 11/2006 | Makower et al. |
| 7,137,990 B2 | 11/2006 | Hebert et al. |
| 7,159,592 B1 | 1/2007 | Makower et al. |
| 7,179,270 B2 | 2/2007 | Makower |
| 7,191,015 B2 | 3/2007 | Lamson et al. |
| 7,229,421 B2 | 6/2007 | Jen et al. |
| 7,316,655 B2 | 1/2008 | Garibotto et al. |
| 7,377,910 B2 * | 5/2008 | Katoh et al. .............. 604/164.13 |
| 7,465,286 B2 | 12/2008 | Patterson et al. |
| 2001/0000041 A1 | 3/2001 | Selmon et al. |
| 2002/0029052 A1 | 3/2002 | Evans et al. |
| 2002/0052637 A1 | 5/2002 | Houser et al. |
| 2002/0103459 A1 | 8/2002 | Sparks et al. |
| 2003/0028200 A1 | 2/2003 | Berg et al. |
| 2003/0040737 A1 | 2/2003 | Merril et al. |
| 2003/0109809 A1 | 6/2003 | Jen et al. |
| 2003/0120195 A1 | 6/2003 | Milo et al. |
| 2003/0236542 A1 | 12/2003 | Makower |
| 2004/0015193 A1 | 1/2004 | Lamson et al. |
| 2004/0059280 A1 | 3/2004 | Makower et al. |
| 2004/0102719 A1 | 5/2004 | Keith et al. |
| 2004/0133225 A1 | 7/2004 | Makower |
| 2004/0158143 A1 | 8/2004 | Flaherty et al. |
| 2004/0167554 A1 | 8/2004 | Simpson et al. |
| 2004/0230156 A1 | 11/2004 | Schreck et al. |
| 2004/0249277 A1 | 12/2004 | Kato et al. |
| 2004/0249338 A1 | 12/2004 | DeCant, Jr. et al. |
| 2005/0038467 A1 | 2/2005 | Hebert et al. |
| 2005/0049574 A1 | 3/2005 | Petrick et al. |
| 2005/0171478 A1 | 8/2005 | Selmon et al. |
| 2005/0177105 A1 | 8/2005 | Shalev |
| 2005/0216044 A1 | 9/2005 | Hong |
| 2005/0261663 A1 | 11/2005 | Patterson et al. |
| 2006/0094930 A1 | 5/2006 | Sparks et al. |
| 2006/0135984 A1 | 6/2006 | Kramer et al. |
| 2006/0229646 A1 | 10/2006 | Sparks |
| 2006/0271078 A1 | 11/2006 | Modesitt |
| 2007/0083220 A1 | 4/2007 | Shamay |
| 2007/0088230 A1 | 4/2007 | Terashi et al. |
| 2007/0093779 A1 * | 4/2007 | Kugler et al. .................. 604/509 |
| 2007/0093780 A1 | 4/2007 | Kugler et al. |
| 2007/0093781 A1 | 4/2007 | Kugler et al. |
| 2007/0093782 A1 | 4/2007 | Kugler et al. |
| 2007/0093783 A1 | 4/2007 | Kugler et al. |
| 2007/0265596 A1 | 11/2007 | Jen et al. |
| 2008/0103443 A1 | 5/2008 | Kabrick et al. |
| 2008/0228171 A1 | 9/2008 | Kugler et al. |
| 2008/0243065 A1 | 10/2008 | Rottenberg et al. |
| 2008/0243067 A1 | 10/2008 | Rottenberg et al. |
| 2009/0088685 A1 | 4/2009 | Kugler et al. |
| 2009/0124899 A1 | 5/2009 | Jacobs et al. |
| 2009/0270890 A1 | 10/2009 | Robinson et al. |
| 2010/0063534 A1 | 3/2010 | Kugler et al. |
| 2010/0069945 A1 | 3/2010 | Olson et al. |

FOREIGN PATENT DOCUMENTS

| | | |
|---|---|---|
| CA | 2 251 685 | 9/1998 |
| EP | 0 820 782 A2 | 1/1998 |
| EP | 0 868 924 A2 | 10/1998 |
| JP | 08257136 A | 10/1996 |
| WO | WO 9839041 | 9/1998 |
| WO | WO 0178822 A2 | 10/2001 |
| WO | WO 2007/033052 A2 | 3/2007 |
| WO | WO 2008/063621 A2 | 5/2008 |
| WO | WO 2009/054943 A1 | 4/2009 |
| WO | WO 2009/100129 A2 | 8/2009 |
| WO | WO 2009/134346 A2 | 11/2009 |
| WO | WO 2010/019241 A1 | 2/2010 |
| WO | WO 2010/044816 A1 | 4/2010 |

OTHER PUBLICATIONS

International Search Report PCT/US2009/033076 issued on Aug. 17, 2009 (6 pages).

Bolia, Amman, *Subintimal Angioplasty: Which Cases to Choose, How to Avoid Pitfalls and Technical Tips*, Combined Session: Vascular Surgery and Interventional Radiology, pp. III 8.1-8.3.

Colombo, Antonio et al., *Treating Chronic Total Occlusions Using Subintimal Tracking and Reentry: The STAR Technique*, Catheterization and Cardiovascular Interventions, vol. 64:407-411 (2005).

* cited by examiner

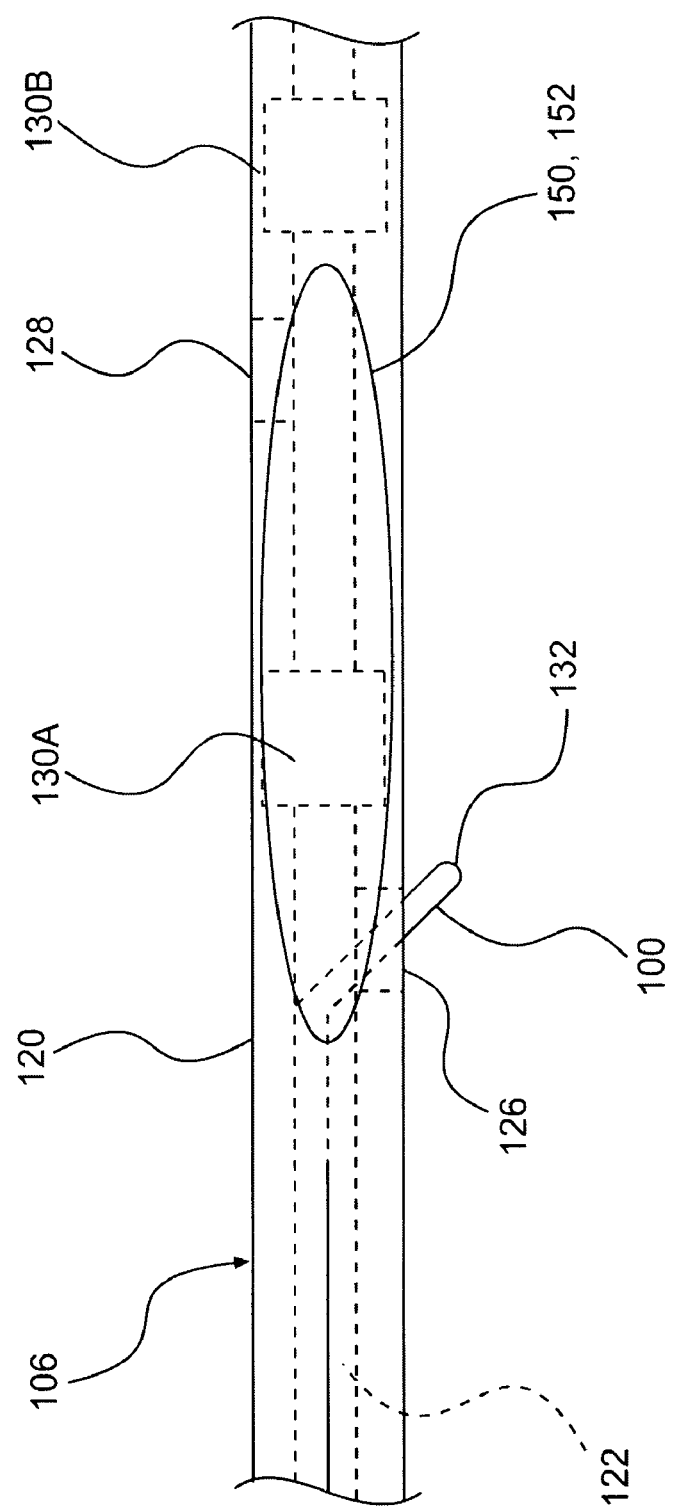

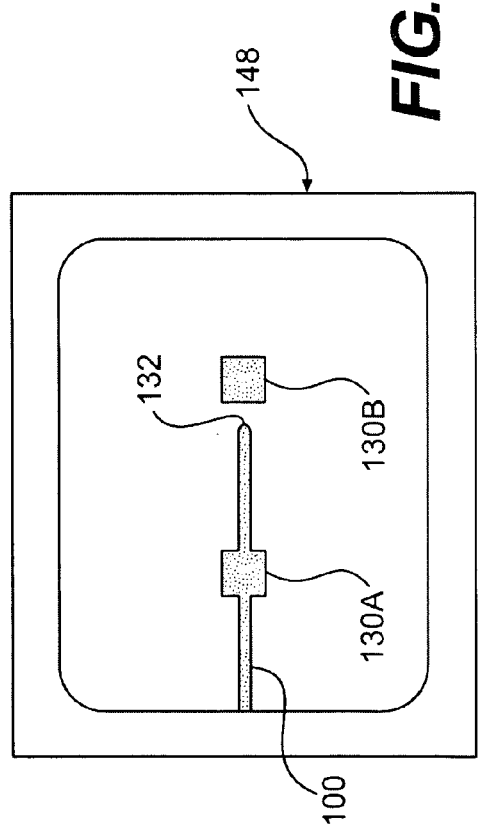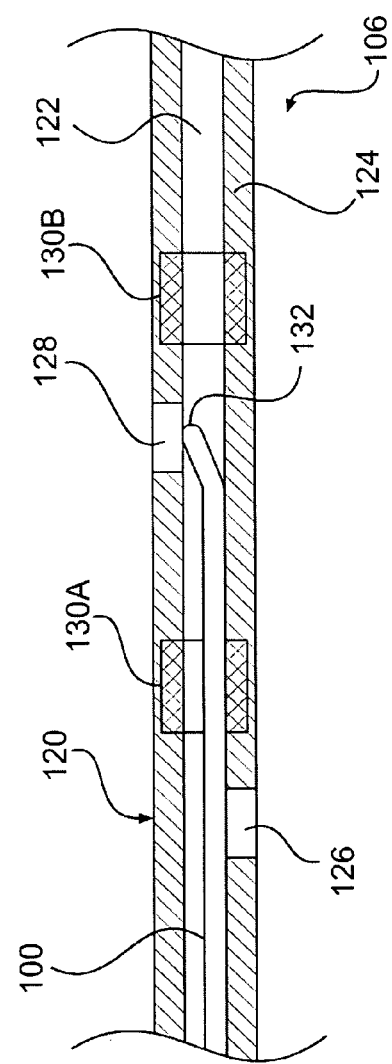

CROSSING OCCLUSIONS IN BLOOD VESSELS

CROSS REFERENCE TO RELATED APPLICATION

This application claims the benefit of U.S. Provisional Application No. 61/063,756, filed Feb. 5, 2008, which is herein incorporated by reference in its entirety.

FIELD OF THE INVENTION

The inventions described herein relate to devices and associated methods for the treatment of chronic total occlusions. More particularly, the inventions described herein relate to devices and methods for crossing chronic total occlusions and establishing a pathway for blood flow past the chronic total occlusions.

BACKGROUND OF THE INVENTION

Due to age, high cholesterol and other contributing factors, a large percentage of the population has arterial atherosclerosis that totally occludes portions of the patient's vasculature and presents significant risks to patient health. For example, in the case of a total occlusion of a coronary artery, the result may be painful angina, loss of cardiac tissue or patient death. In another example, complete occlusion of the femoral and/or popliteal arteries in the leg may result in limb threatening ischemia and limb amputation.

Commonly known endovascular devices and techniques are either inefficient (time consuming procedure), have a high risk of perforating a vessel (poor safety) or fail to cross the occlusion (poor efficacy). Physicians currently have difficulty visualizing the native vessel lumen, can not accurately direct endovascular devices toward the visualized lumen, or fail to advance devices through the lesion. Bypass surgery is often the preferred treatment for patients with chronic total occlusions, but less invasive techniques would be preferred.

Described herein are devices and methods employed to exploit the vascular wall of a vascular lumen for the purpose of bypassing a total occlusion of an artery. Exploitation of a vascular wall may involve the passage of an endovascular device into and out of said wall which is commonly and interchangeable described as false lumen access, intramural access, submedial access or in the case of this disclosure, subintimal access.

SUMMARY OF THE INVENTION

Described herein are devices and methods employed to exploit the vascular wall of a vascular lumen for the purpose of bypassing a total occlusion of an artery. Exploitation of a vascular wall may involve the passage of an endovascular device into and out of said wall which is commonly and interchangeable described as false lumen access, intramural access, submedial access or in the case of this disclosure, subintimal access.

In one aspect, the present disclosure is directed a method of facilitating treatment via a vascular wall defining a vascular lumen containing an occlusion therein. The method may include providing a first intravascular device having a distal portion and at least one aperture and positioning the distal portion of the first intravascular device in the vascular wall. The method may further include providing a reentry device having a body and a distal tip, the distal tip having a natural state and a compressed state and inserting the distal tip, in the compressed state, in the distal portion of the first intravascular device. The method may further include advancing the distal tip, in the natural state, through the at least one aperture of the first intravascular device.

In another aspect, the present disclosure is directed an apparatus for facilitating treatment via a vascular wall defining a vascular lumen containing an occlusion therein. The apparatus may include a first intravascular device having a distal portion, the distal portion including at least one aperture, at least one radiopaque marker, and at least one orienting element. The apparatus may further include a reentry device having a body and a distal tip, the distal tip having a natural state and a compressed state.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

FIG. 16 has a different scale than the previous figure so that more of the surrounding context is visible in FIG. 16.

FIG. 24 is a plan view including the orienting device shown in the previous figure. In FIG. 24, a distal portion of a re-entry device can be seen extending through an aperture of the orienting device.

FIG. 25A is a cross-sectional view of an orienting device including a radiopaque marker.

FIG. 25B is a representation of a fluoroscopic display. The radiopaque marker of the orienting device shown in the previous figure is visible in this fluoroscopic display. A radiopaque re-entry device is also visible in this display.

In FIG. 28, an orienting device is shown disposed between the adventitia and the intima.

DESCRIPTION OF THE EMBODIMENTS

Reference will now be made in detail to the present embodiments of the invention, examples of which are illustrated in the accompanying drawings. Wherever possible, the same reference numbers will be used throughout the drawings to refer to the same or like parts.

The following detailed description should be read with reference to the drawings in which similar elements in different drawings are numbered the same. The drawings, which are not necessarily to scale, depict illustrative embodiments and are not intended to limit the scope of the invention.

Figure 1:
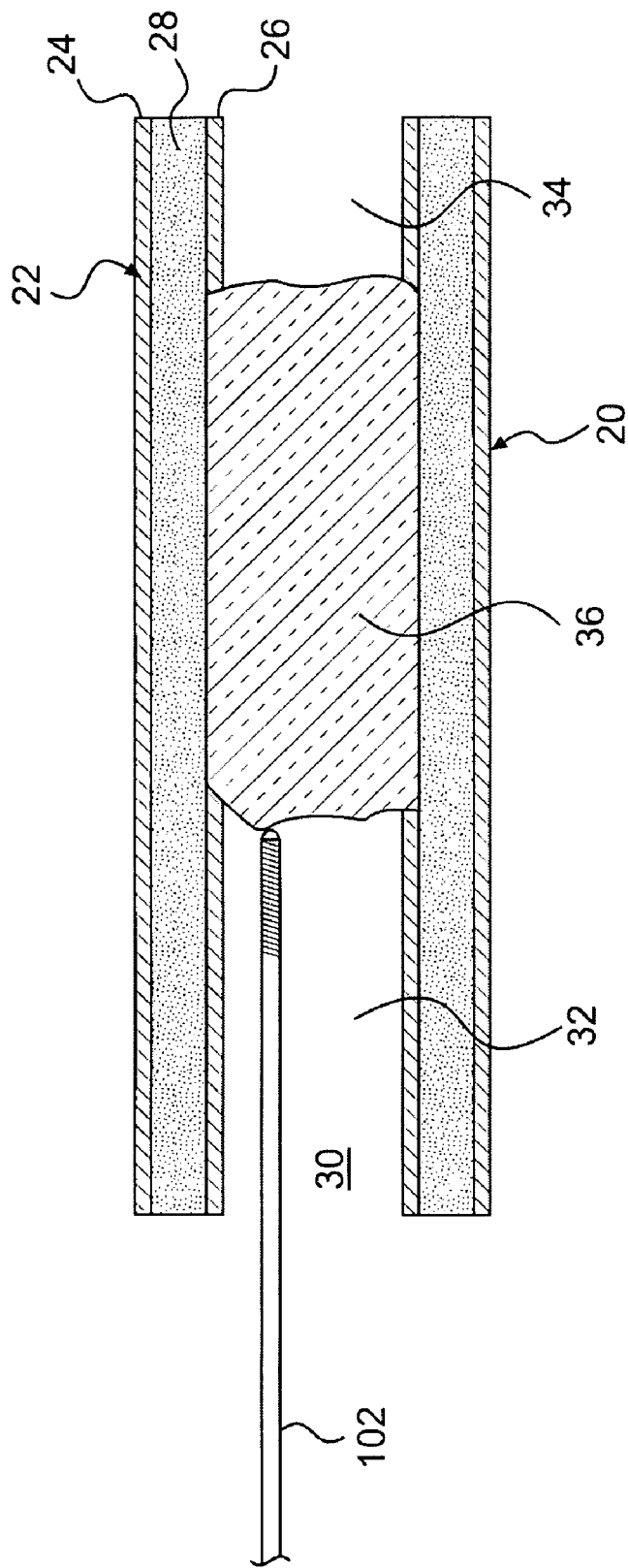
FIG. 1 is a cross-sectional view of an artery with a wall having three layers. The outermost layer of the wall is the adventitia and the innermost layer is the intima. The tissues extending between the intima and the adventitia may be collectively referred to as the media.

FIG. 1 is a cross-sectional view of an artery 20 having a wall 22. In FIG. 1, wall 22 of artery 20 is shown having three layers. The outermost layer of wall 22 is the adventitia 24 and the innermost layer of wall 22 is the intima 26. The tissues extending between intima 26 and adventitia 24 may be collectively referred to as the media 28. For purposes of illustration, intima 26, media 28 and adventitia 24 are each shown as a single homogenous layer in FIG. 1. In the human body, however, the intima and the media each comprise a number of sub-layers. The transition between the external most portion of the intima and the internal most portion of the media is sometimes referred to as the subintimal space. Intima 26 defines a true lumen 30 of artery 20. In FIG. 1, an occlusion 36 is shown blocking true lumen 30. Occlusion 36 divides true lumen 30 into a proximal segment 32 and a distal segment 34. In FIG. 1, a distal portion of a guidewire 102 is shown extending into proximal segment 32 of true lumen 30.

As shown in FIG. 1, methods described in this document may include the step of advancing a guidewire to a location proximate an occlusion in a blood vessel. The exemplary methods described in this document may also include the step of advancing guidewire 102 between occlusion 36 and adventitia 24. In some cases, however, the nature of the occlusion and the blood vessel will be such that the guidewire is unlikely to advance beyond the occlusion.

Figure 2:
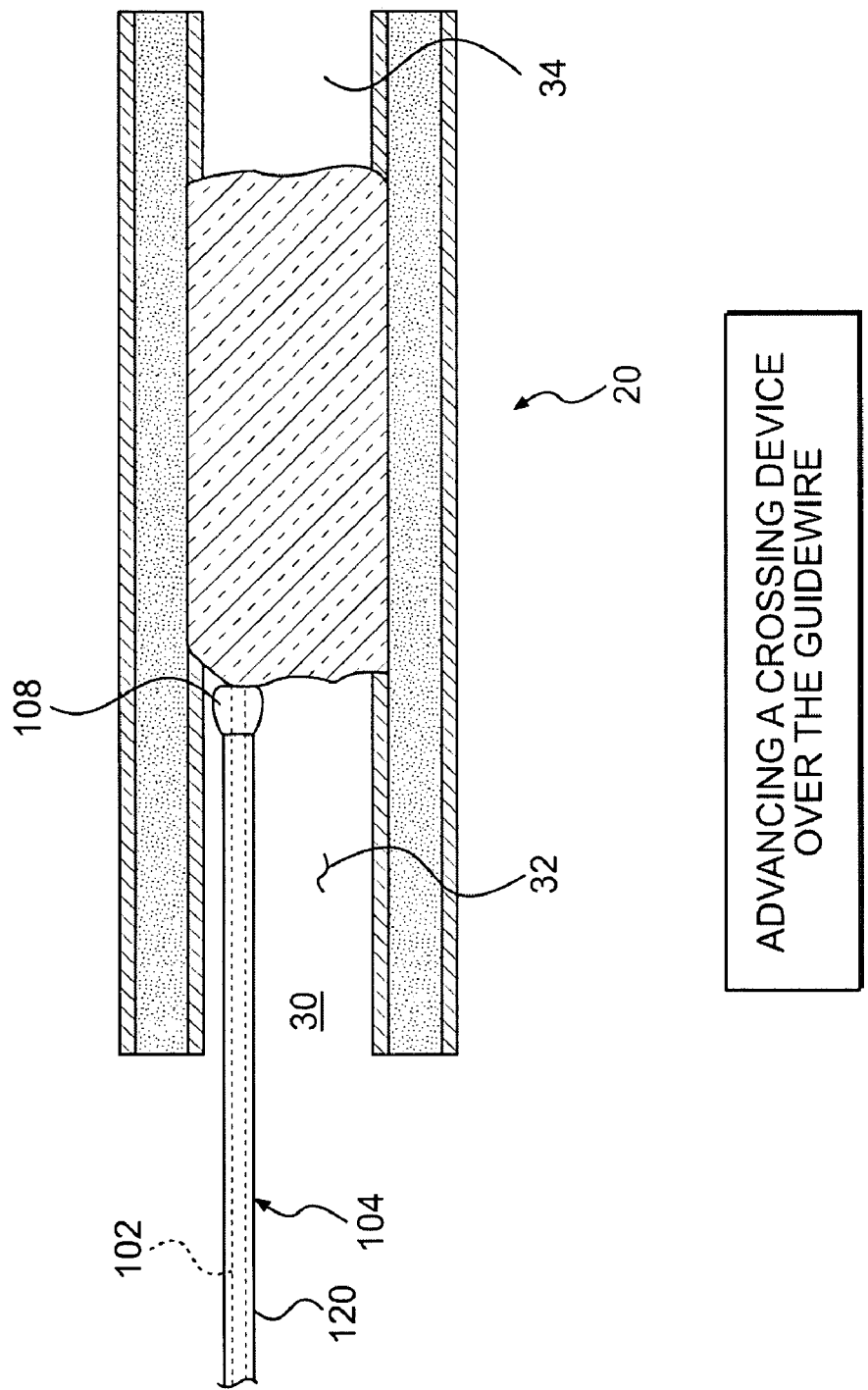
FIG. 2 is an additional view of the artery shown in the previous figure in which a crossing device has been advanced over guidewire so that a distal portion of the crossing device is disposed in a proximal segment of a true lumen of the artery.

FIG. 2 is an additional view of artery 20 shown in the previous figure. In the embodiment of FIG. 2, a crossing device 104 has been advanced over guidewire 102 so that a distal portion of crossing device 104 is disposed in proximal segment 32 of true lumen 30. Crossing device 104 may be used to establish a channel between proximal segment 32 and distal segment 34. Crossing device 104 of FIG. 2 comprises a tip 108 that is fixed to a distal end of a shaft 120. As shown in FIG. 2, methods described in this document may include the step of advancing a crossing device over a guidewire.

Figure 3:
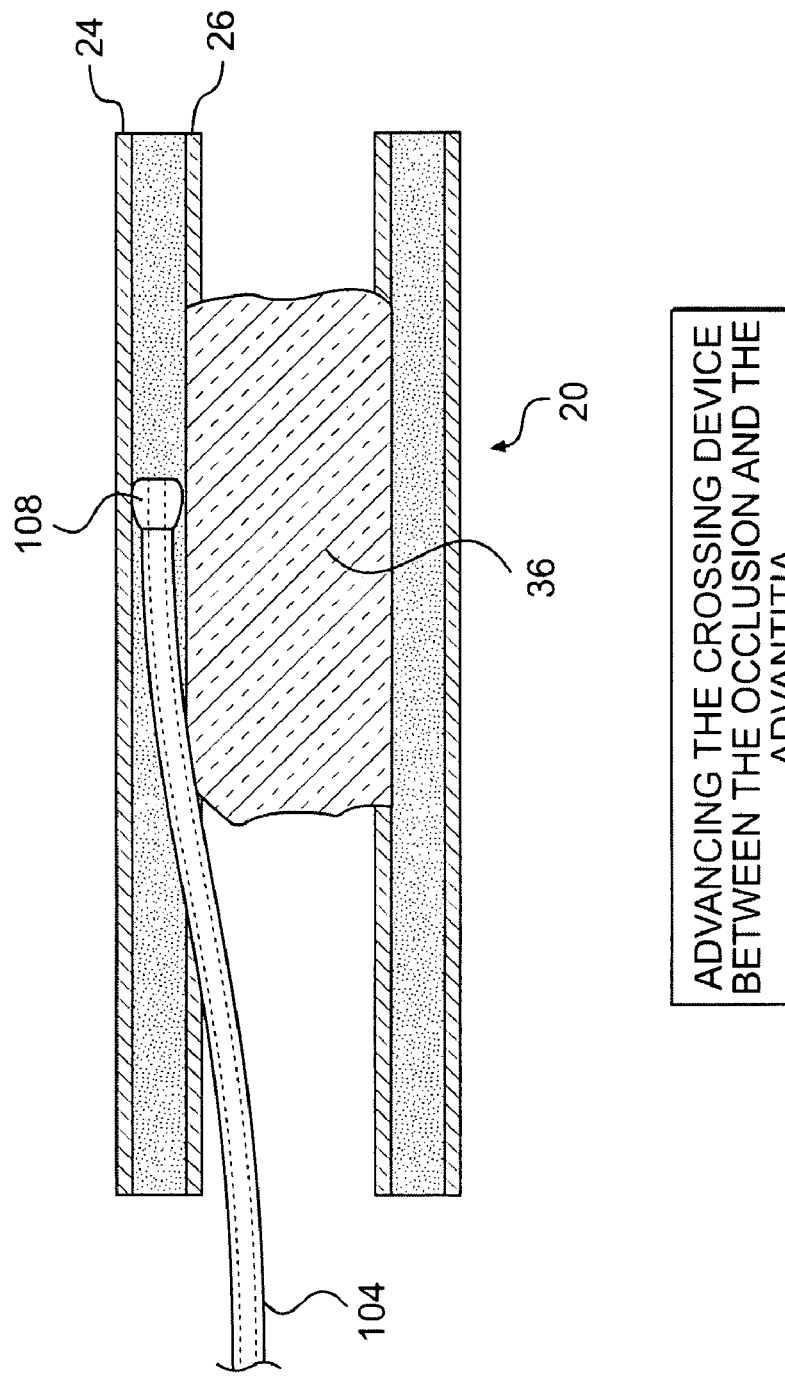
FIG. 3 is an additional view of the artery shown in the previous figure in which the distal end of the crossing device has been advanced in a distal direction so that a tip of the crossing device is adjacent to an occlusion.

FIG. 3 is an additional view of artery 20 shown in the previous figure. In the embodiment of FIG. 3, the distal end of crossing device 104 has been advanced in a distal direction so that tip 108 is adjacent to occlusion 36. With reference to FIG. 3, it will be appreciated that tip 108 has passed through intima 26 and is disposed between occlusion 36 and adventitia 24 of artery 20. Some methods described in this document may include the step of advancing a crossing device between an occlusion and the adventitia of an artery.

Figure 4:
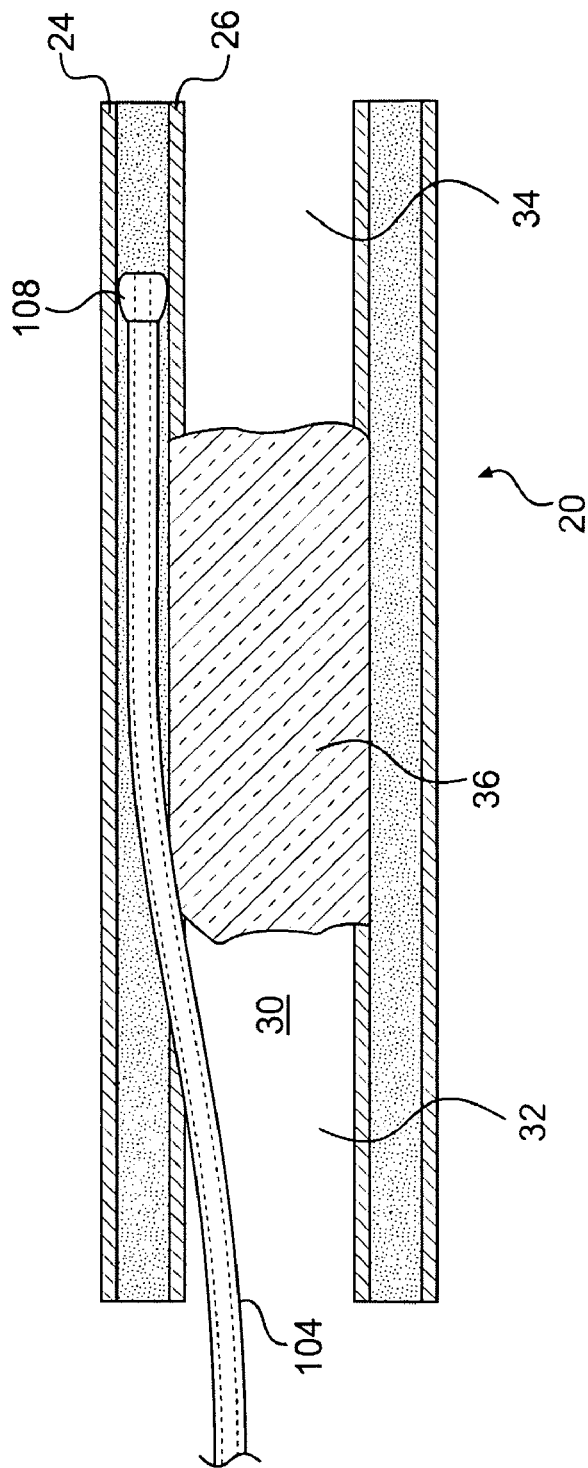
FIG. 4 is an additional view of the artery and crossing device shown in the previous figure. In the embodiment of FIG. 4, the distal end of the crossing device has been advanced in an axial direction past the occlusion.

FIG. 4 is an additional view of artery 20 and crossing device 104 shown in the previous figure. In the embodiment of FIG. 4, the distal end of crossing device 104 has been advanced in an axial direction past occlusion 36. Accordingly, it will be appreciated that methods described in this document may include the step of advancing a crossing device beyond an occlusion.

In the embodiment of FIG. 4, crossing device has crossed occlusion 36 by advancing between occlusion 36 and adventitia 24 of artery 20. It is to be appreciated that other methods of crossing an occlusion are within the spirit and scope of this disclosure. For example, the crossing device 104 may pass through occlusion 36 while remaining disposed inside true lumen 30.

In FIG. 4, tip 108 of crossing device 104 is shown residing between intima 26 and adventitia 24 of artery 20. As tip 108 moves in an axial direction between intima 26 and adventitia 24, tip 108 may cause blunt dissection of the layers forming the wall of artery 20. Alternatively, tip 108 may cause blunt dissection of the materials comprising the occlusion 36.

In some useful methods in accordance with the present disclosure, crossing device 104 is rotated about its longitudinal axis and moved in a direction parallel to its longitudinal axis simultaneously. When this is the case, rotation of crossing device 104 may reduce resistance to the axial advancement of crossing device 104. These methods take advantage of the fact that the kinetic coefficient of friction is usually less than the static coefficient of friction for a given frictional interface. Rotating crossing device 104 assures that the coefficient of friction at the interface between the crossing device and the surround tissue will be a kinetic coefficient of friction and not a static coefficient of friction.

With reference to FIG. 4, it will be appreciated that crossing device 104 extends past occlusion 36. In FIG. 4, occlusion 36 is shown blocking a true lumen 30. Occlusion 36 divides true lumen 30 into a proximal segment 32 and a distal segment 34. When a crossing device in accordance with some embodiments of the present disclosure is advanced through the subintimal space of an artery, the distal end of the crossing device may penetrate the intima and enter the distal segment of the true lumen after advancing beyond an occlusion. When this is the case, fluid communication between the proximal segment and the distal segment may be achieved via a channel created by the crossing device.

Figure 5:
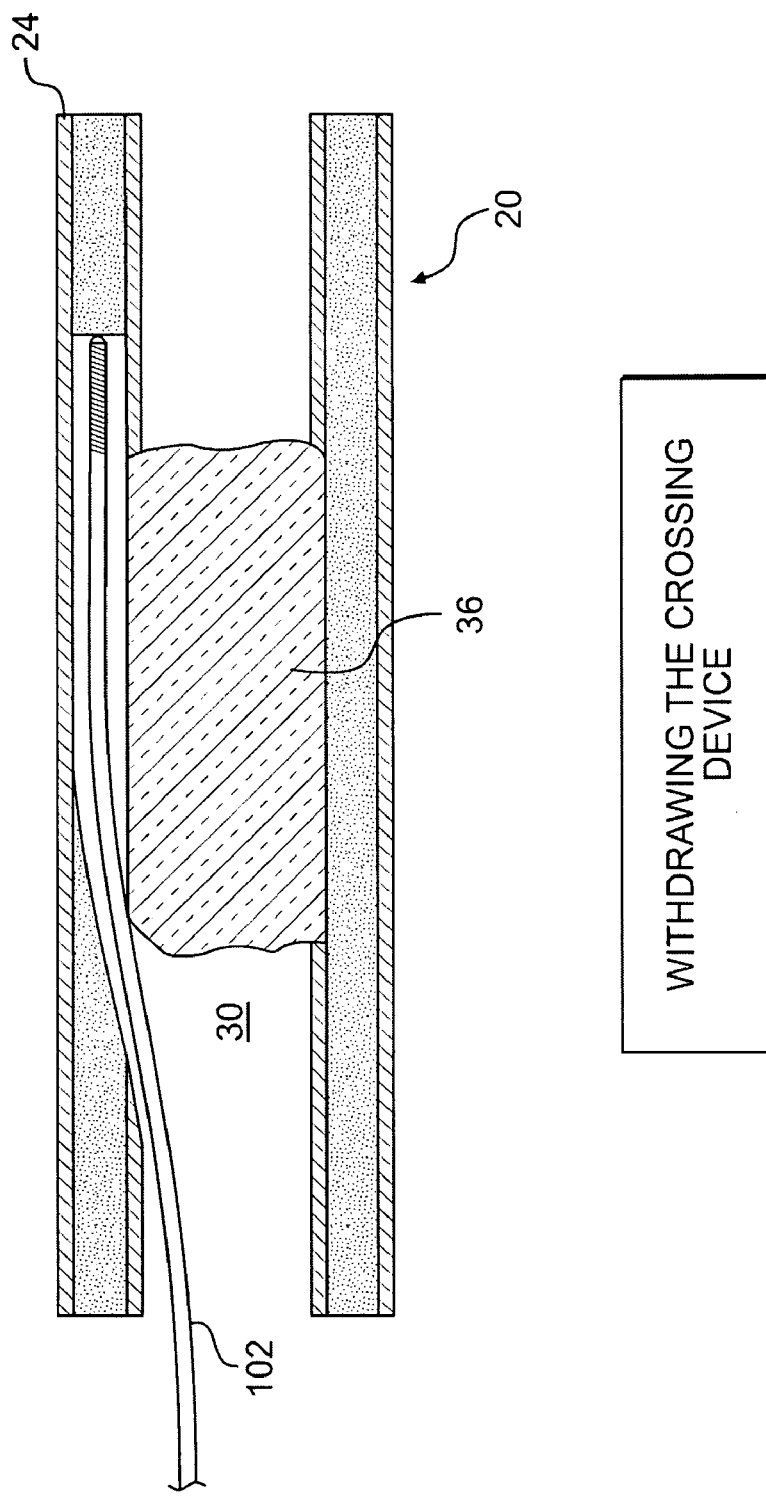
FIG. 5 is a view of the artery shown in the previous figure showing that the crossing device has been withdrawn from the true lumen of the artery.

FIG. 5 is an additional view of artery 20 shown in the previous figure. In the embodiment of FIG. 5, crossing device 104 has been withdrawn from true lumen 30 of artery 20. With reference to FIG. 5, it will be appreciated that guidewire 102 remains in the position formerly occupied by crossing device 104.

The position of guidewire 102 shown in FIG. 5 may be achieved using crossing device 104. Guidewire 102 may be positioned, for example, by first placing crossing device 104 in the position shown in the previous figure, then advancing guidewire 102 through lumen 122 defined by shaft 120 of crossing device 104. Alternately, guidewire 102 may be disposed within lumen 122 while crossing device 104 is advanced beyond occlusion 36.

With guidewire 102 in the position shown in FIG. 5, guidewire 102 may be used to direct other devices between occlusion 36 and adventitia 24. For example, a catheter may be advanced over guidewire 102 until the distal end of the catheter extends between an occlusion and the adventia. After reaching this location, the catheter may be used to dilate the tissue surrounding the catheter. Examples of catheters that may be used to dilate tissue include balloon catheters and atherectomy catheters.

Figure 6:
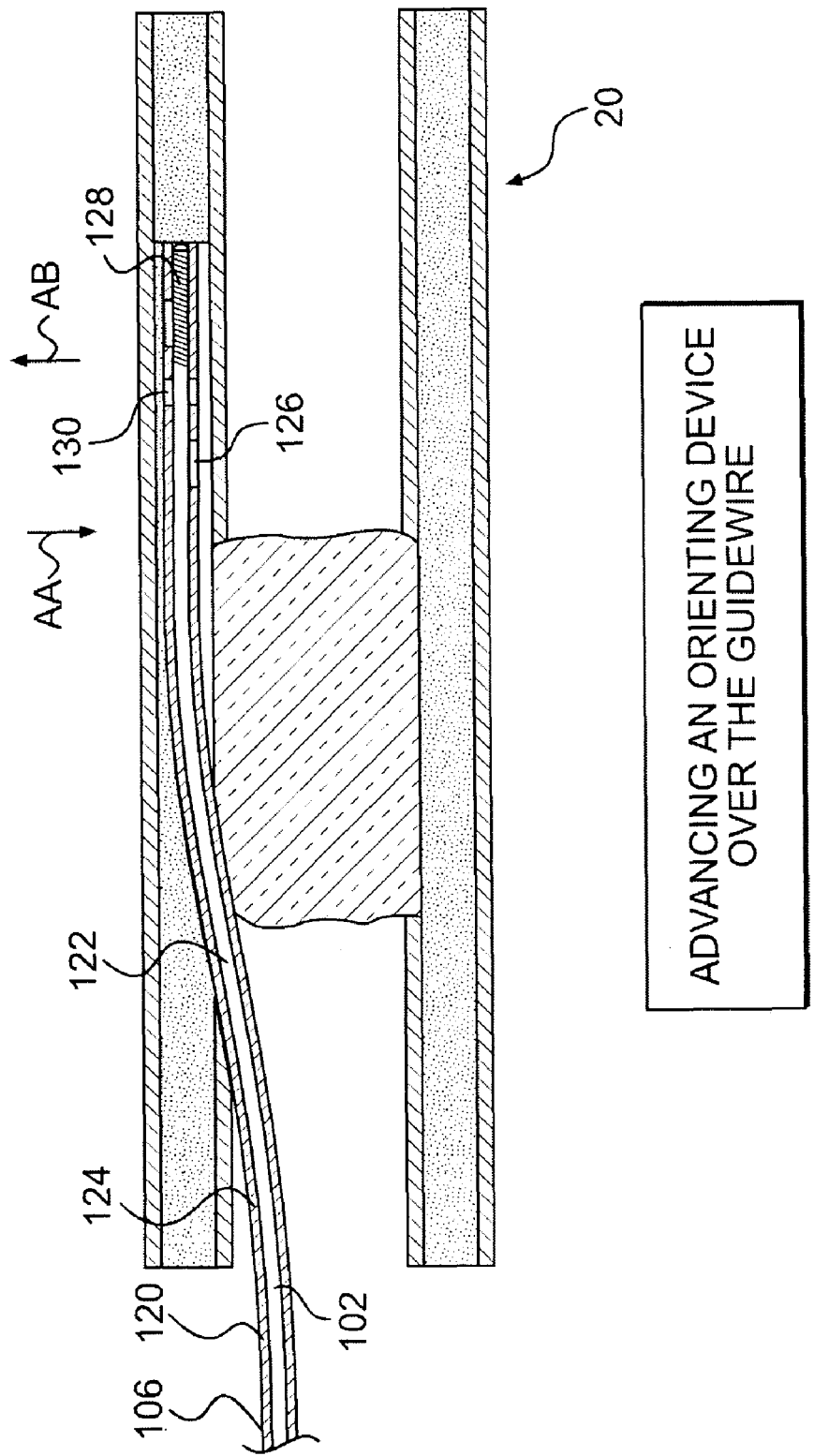
FIG. 6 is an additional view of the artery and the guidewire shown in the previous figure. In the embodiment of FIG. 6, an orienting device has been advanced over the guidewire.

FIG. 6 is an additional view of artery 20 and guidewire 102 shown in the previous figure. In the embodiment of FIG. 6, an orienting device 106 has been advanced over guidewire 102. Orienting device 106 includes a shaft 120 comprising a wall 124 defining a lumen 122. A first aperture 126 and a second aperture 128 are also defined by wall 124. In the embodiment of FIG. 6, first aperture 126 and second aperture 128 are both in fluid communication with lumen 122.

In the embodiment of FIG. 6, orienting device 106 has been positioned so that first aperture 126 opens toward intima 26 of artery 20 and second aperture 128 opens toward adventitia 24. With reference to FIG. 6, it will be appreciated that first aperture extends in a first direction that is represented by a first arrow AA and second aperture extends in a second direction that is represented by a second arrow AB.

In FIG. 6, first arrow AA and second arrow AB are used to illustrate the fact that the second direction is general opposite the first direction. In the embodiment of FIG. 6, first arrow AA and second arrow AB are orient 180 degrees away from each other. In the embodiment of FIG. 6, first aperture 126 and second aperture 128 are longitudinally separated from one another. Orienting device 106 includes a radiopaque marker 130 that is located between first aperture 126 and second aperture 128.

Figure 7:
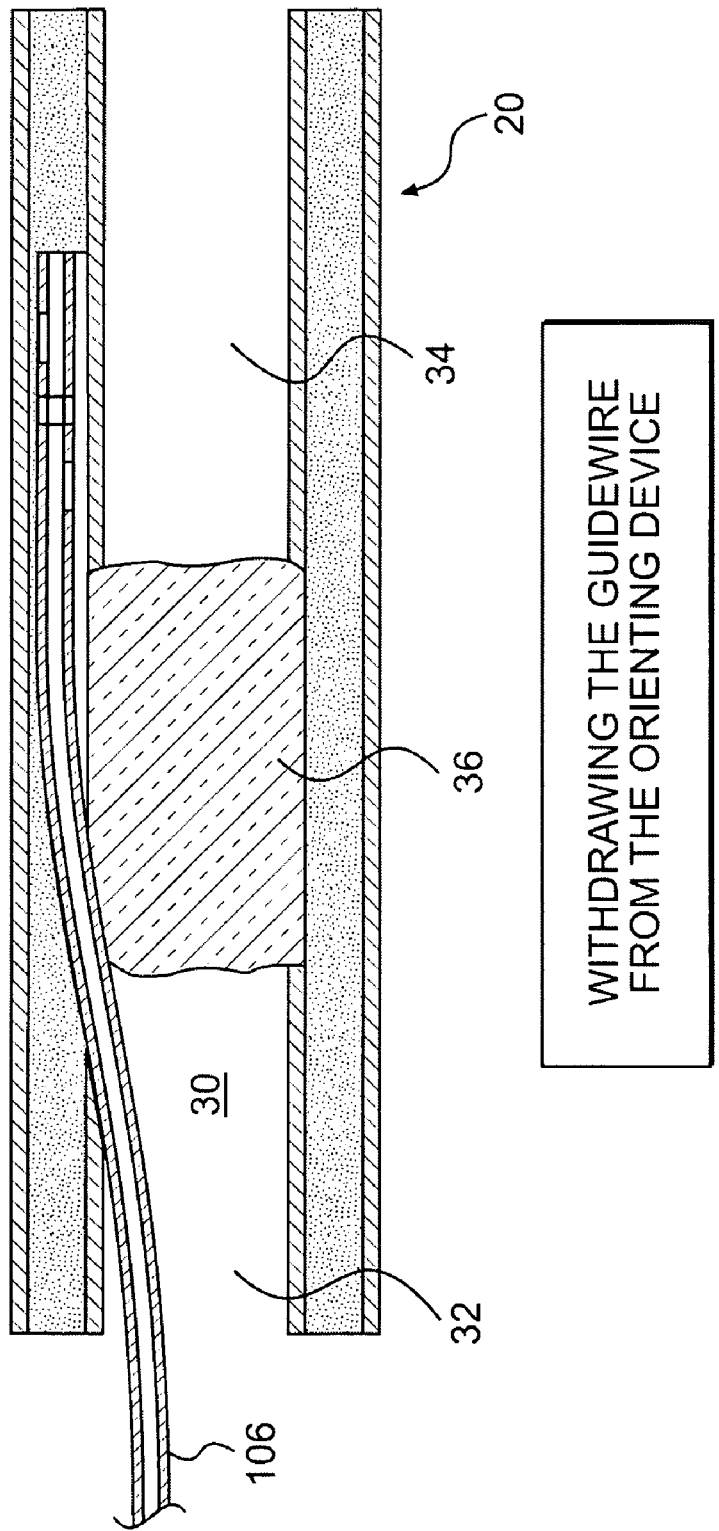
FIG. 7 is an additional view of the artery and the orienting device shown in the previous figure. In the embodiment of FIG. 7, the guidewire has been withdrawn leaving the orienting device in the position shown in FIG. 7.

FIG. 7 is an additional view of artery 20 and orienting device 106 shown in the previous figure. In the embodiment of FIG. 7, guidewire 102 has been withdrawn leaving orienting device 106 in the position shown in FIG. 7. With reference to FIG. 7, it will be appreciated that orienting device 106 extends beyond occlusion 36. In FIG. 7, occlusion 36 is shown blocking true lumen 30. Occlusion 36 divides true lumen 30 into a proximal segment 32 and a distal segment 34. When an orienting device in accordance with some embodiments disclosed herein is advanced between the adventitia and the intima of an artery, the orienting device may be used to direct a re-entry device toward true lumen 30. Fluid communication between proximal segment 32 and distal segment 34 may be achieved by re-entering the true lumen with the re-entry device.

Figure 8:
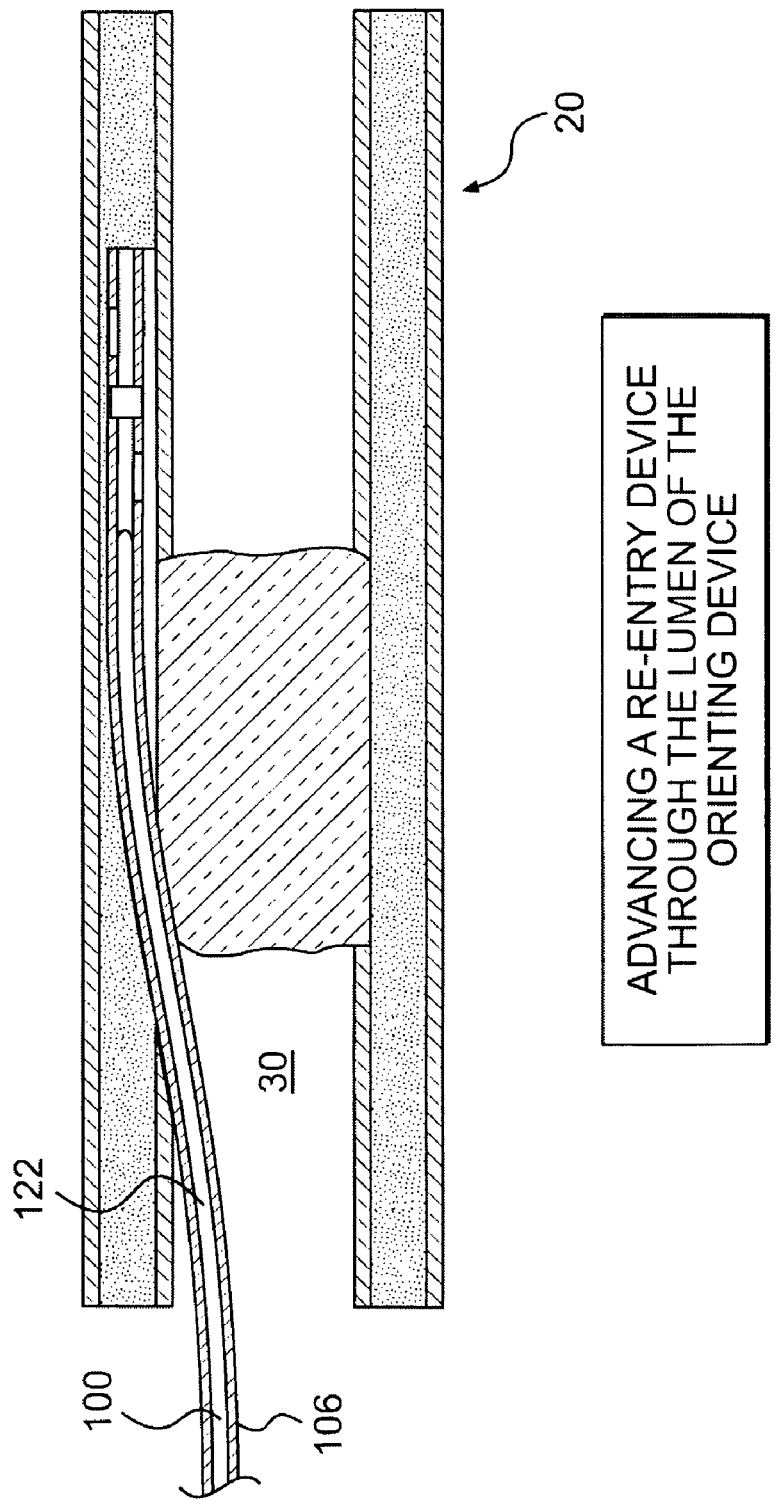
FIG. 8 is an additional view of the artery and the orienting device shown in the previous figure. In the embodiment of FIG. 8, a re-entry device has been advanced into the lumen of the orienting device.

FIG. 8 is an additional view of artery 20 and orienting device 106 shown in the previous figure. In the embodiment of FIG. 8, a re-entry device 100 has been advanced into lumen 122 of orienting device 106. Some useful methods include the step of advancing the distal end of re-entry device 100 into true lumen 30.

Figure 9:
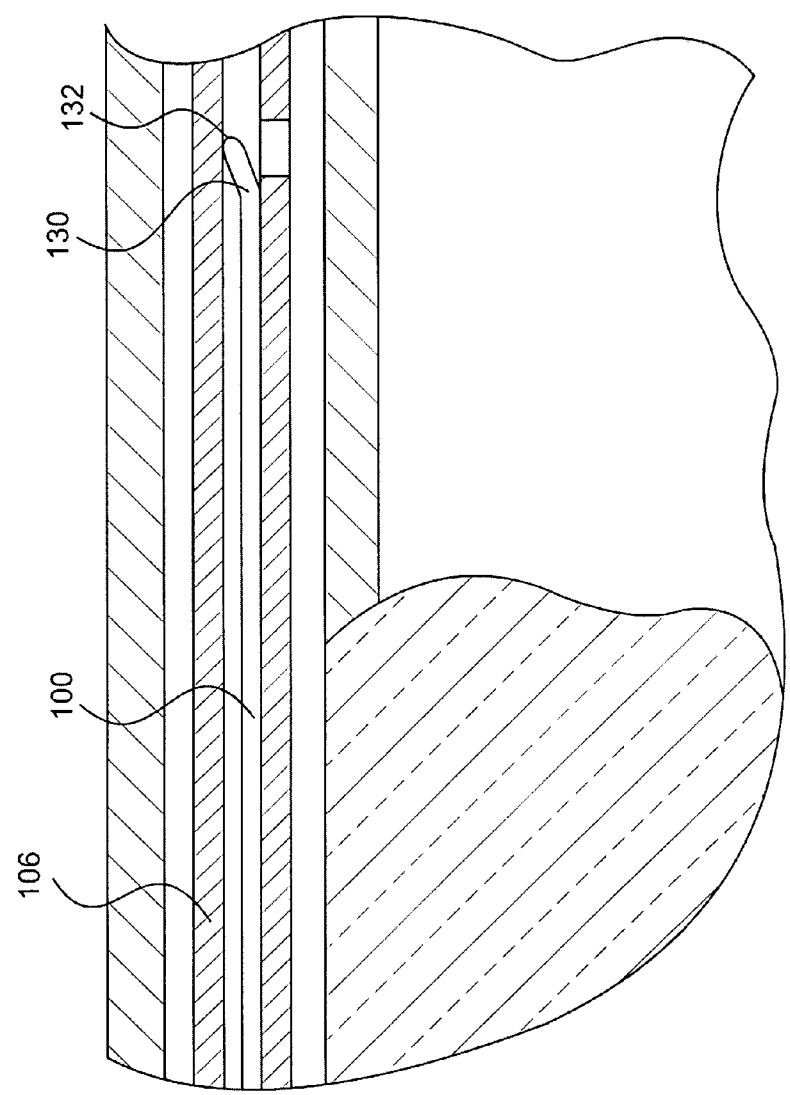
FIG. 9 is an enlarged partial cross-sectional view showing a portion of the re-entry device and the orienting device shown in the previous figure.

FIG. 9 is an enlarged partial cross-sectional view showing a portion of re-entry device 100 and orienting device 106 shown in the previous figure. With reference to FIG. 9, it will be appreciated that re-entry device 100 includes a bend 130 near distal end 132 of re-entry device 100.

Figure 10:
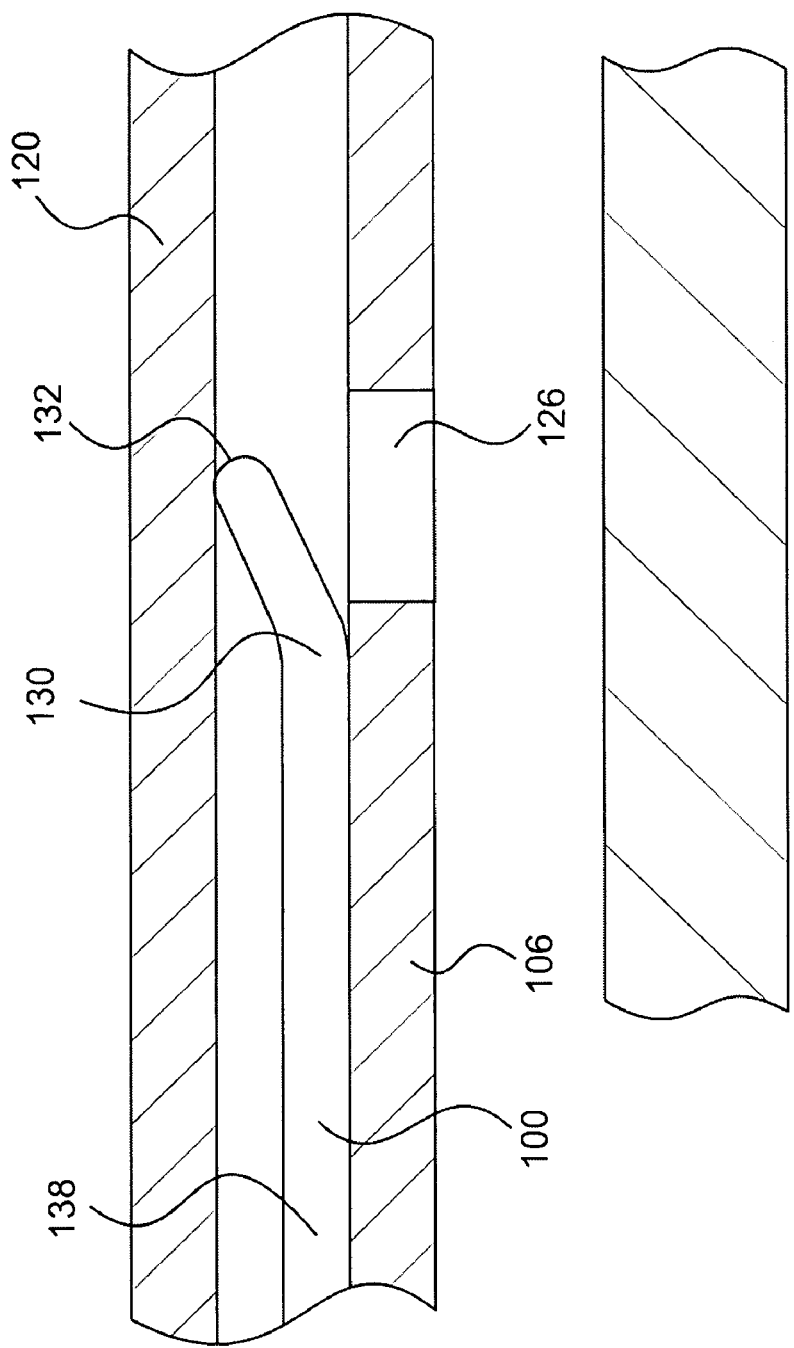
FIG. 10 is an additional partial cross-sectional view showing a portion of the re-entry device and the orienting device shown in the previous figure.

FIG. 10 is an additional partial cross-sectional view showing a portion of re-entry device 100 and orienting device 106. FIG. 10 is further enlarged and simplified relative to the items shown in the previous figure. In the embodiment of FIG. 10, a body 138 of re-entry device 100 is biased to assume a bent shape including a bend 130. Also in the embodiment of FIG. 10, shaft 120 of orienting device 106 is holding re-entry device 100 in a somewhat compressed state. When this is the case, re-entry device 100 can be inserted through first aperture 126 by positioning distal end 132 over first aperture 126 and allowing bend 130 to assume it's natural state (i.e., bent at a sharper angle). Re-entry device 100 can be inserted through aperture 126 until it comes into contact with intima 26.

It the embodiment of FIG. 10, distal end 132 of core 136 is axially aligned with first aperture 126, however, bend 130 is causing distal end 132 to point away from first aperture 126. When this is the case, distal end 132 may be positioned over first aperture 126 by rotating core 136.

Figure 11:
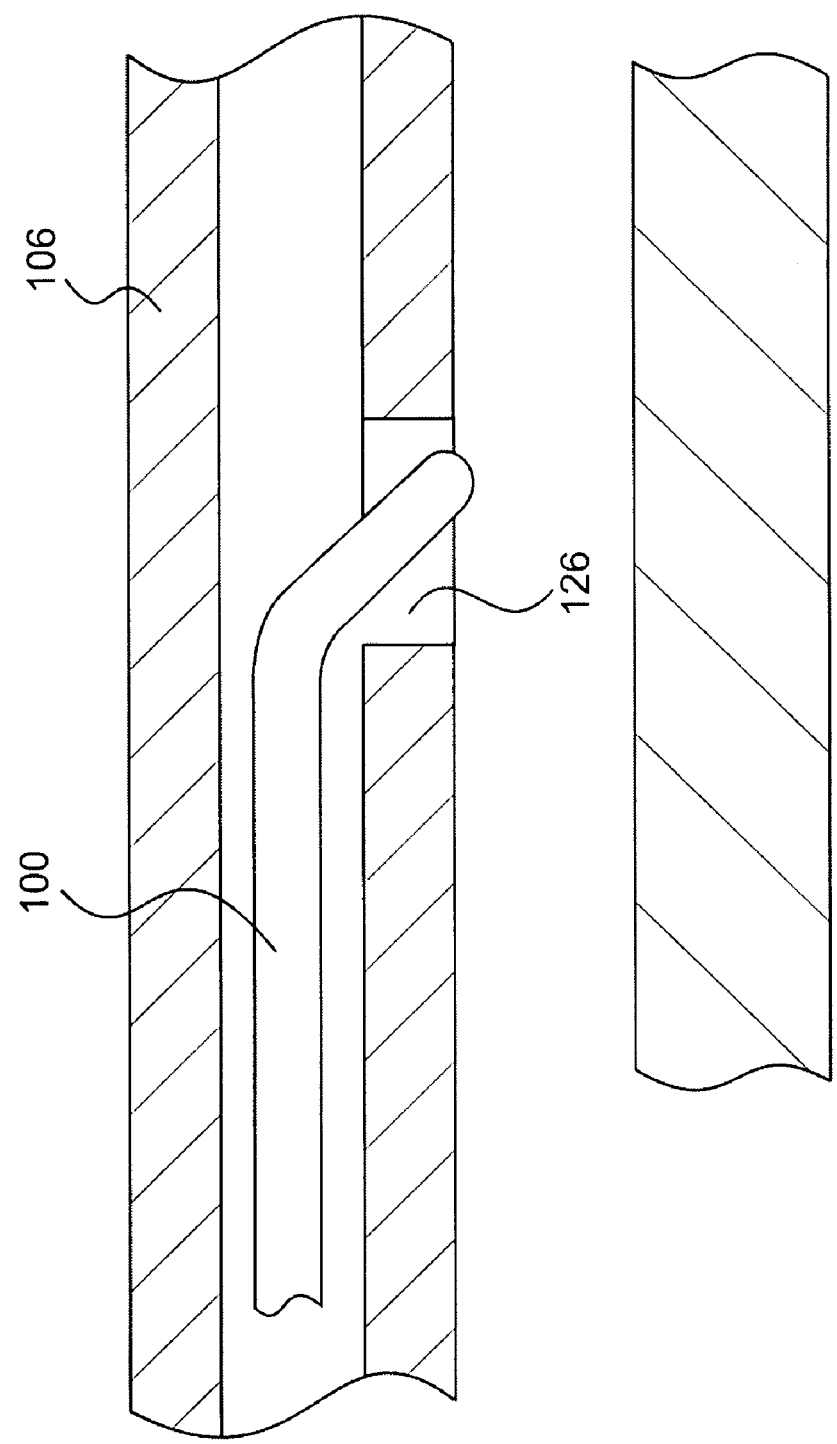
FIG. 11 is an enlarged partial cross-sectional view showing a portion of the re-entry device and the orienting device shown in the previous figure.

FIG. 11 is an enlarged partial cross-sectional view showing a portion of re-entry device 100 and orienting device 106 shown in the previous figure. In the embodiment of FIG. 11, re-entry device 100 has been positioned so that a distal portion of re-entry device 100 has entered first aperture 126. Intima 26 is shown below first aperture 126 in FIG. 11.

Figure 12:
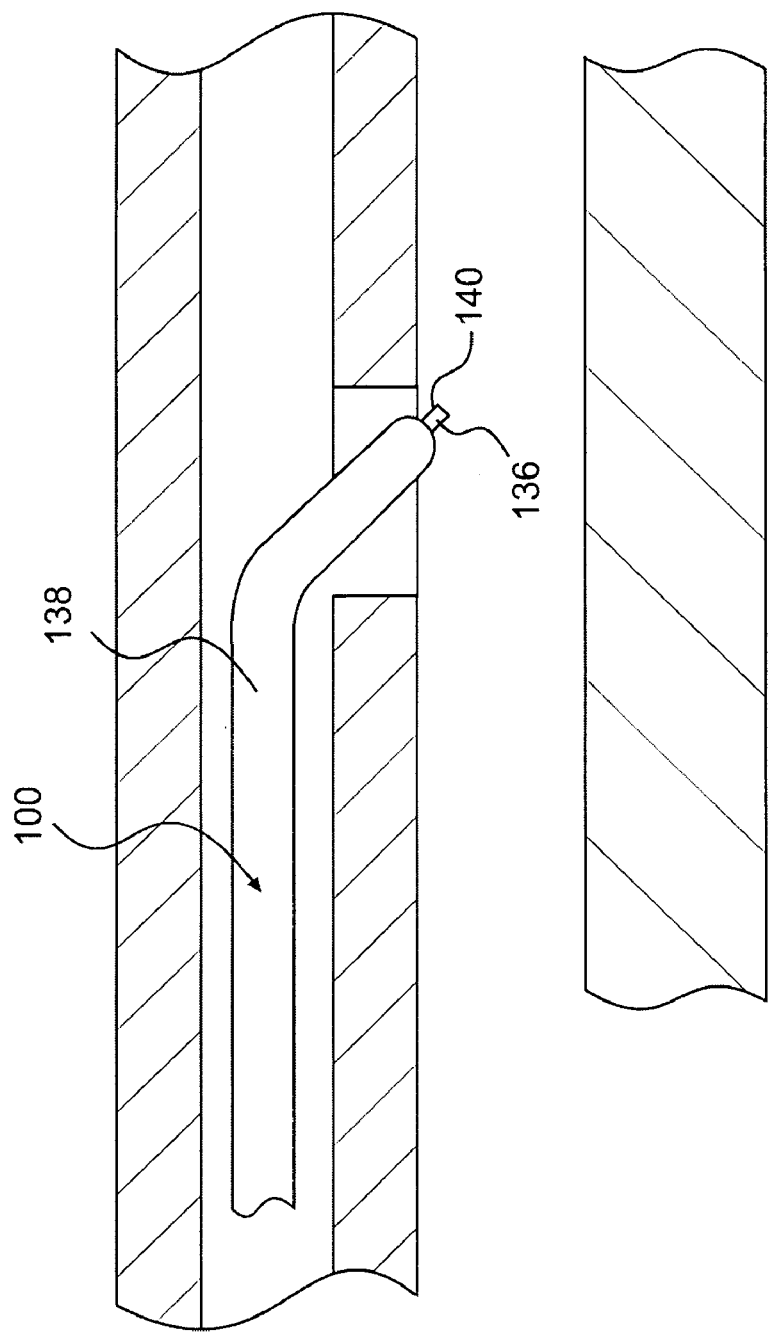
FIG. 12 is another enlarged partial cross-sectional view showing a portion of the re-entry device shown in the previous figure. In the embodiment of FIG. 12, a core of the re-entry device has been advanced so that a portion of the core extends beyond the body of the re-entry device.

FIG. 12 is an enlarged partial cross-sectional view showing a portion of re-entry device 100 and intima 26. With reference to FIG. 12, it will be appreciated that re-entry device 100 comprises a body 138 and a core 136. In the embodiment of FIG. 12, core 136 has been advanced so that a portion of core 136 extends beyond body 138. For purposes of illustration and exposition, the portion of core 136 extending beyond body 138 is referred to as a penetrator 140. Embodiments of re-entry device 100 are contemplated in which penetrator 140 is fixed in the position shown in FIG. 12.

Figure 13:
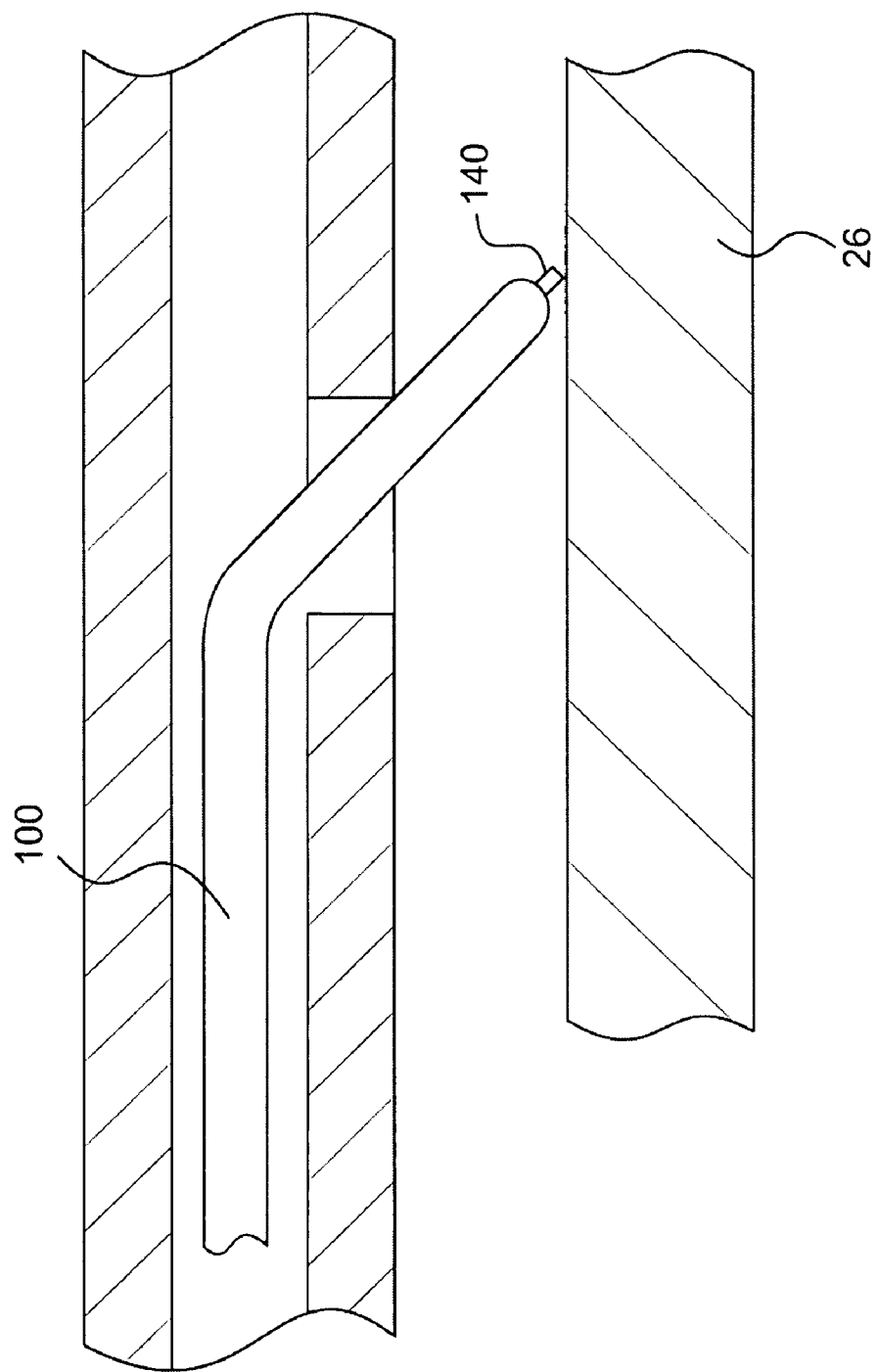
FIG. 13 is an additional enlarged partial cross-sectional view showing a portion of the re-entry device shown in the previous figure. In the embodiment of FIG. 13, the re-entry device has been advanced so that a penetrator is contacting the intima of an artery.

FIG. 13 is an enlarged partial cross-sectional view showing a portion of re-entry device 100. In the embodiment of FIG. 13, re-entry device 100 has been advanced so that penetrator 140 is shown contacting intima 26 in FIG. 13.

Figure 14:
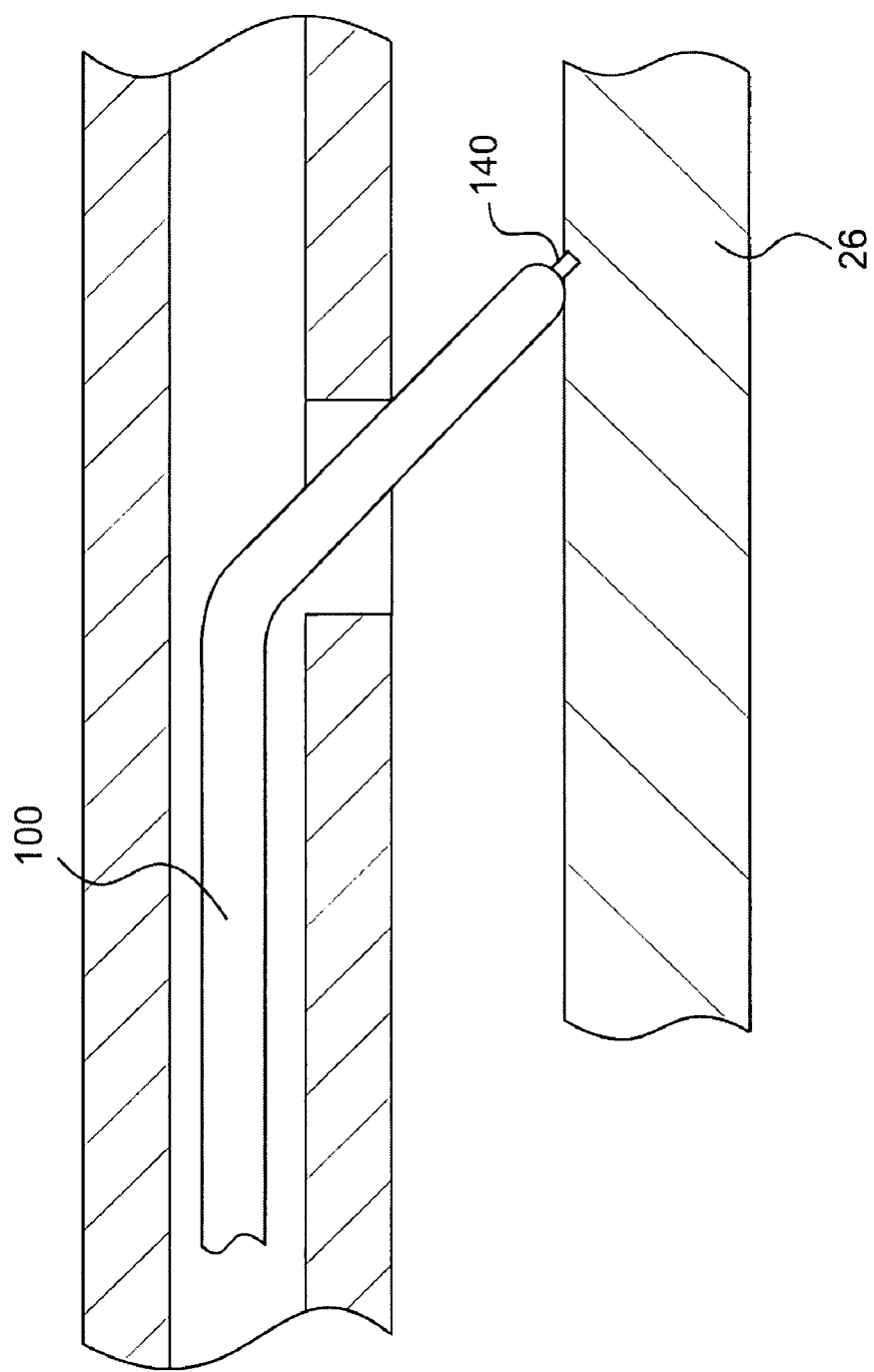
FIG. 14 is yet another enlarged partial cross-sectional view showing a portion of the re-entry device shown in the previous figure. In the embodiment of FIG. 14, the penetrator of the re-entry device has pierced the intima.

FIG. 14 is an enlarged partial cross-sectional view showing a portion of re-entry device 100. In the embodiment of FIG. 14, penetrator 140 of re-entry device 100 has pierced intima 26.

Figure 15:
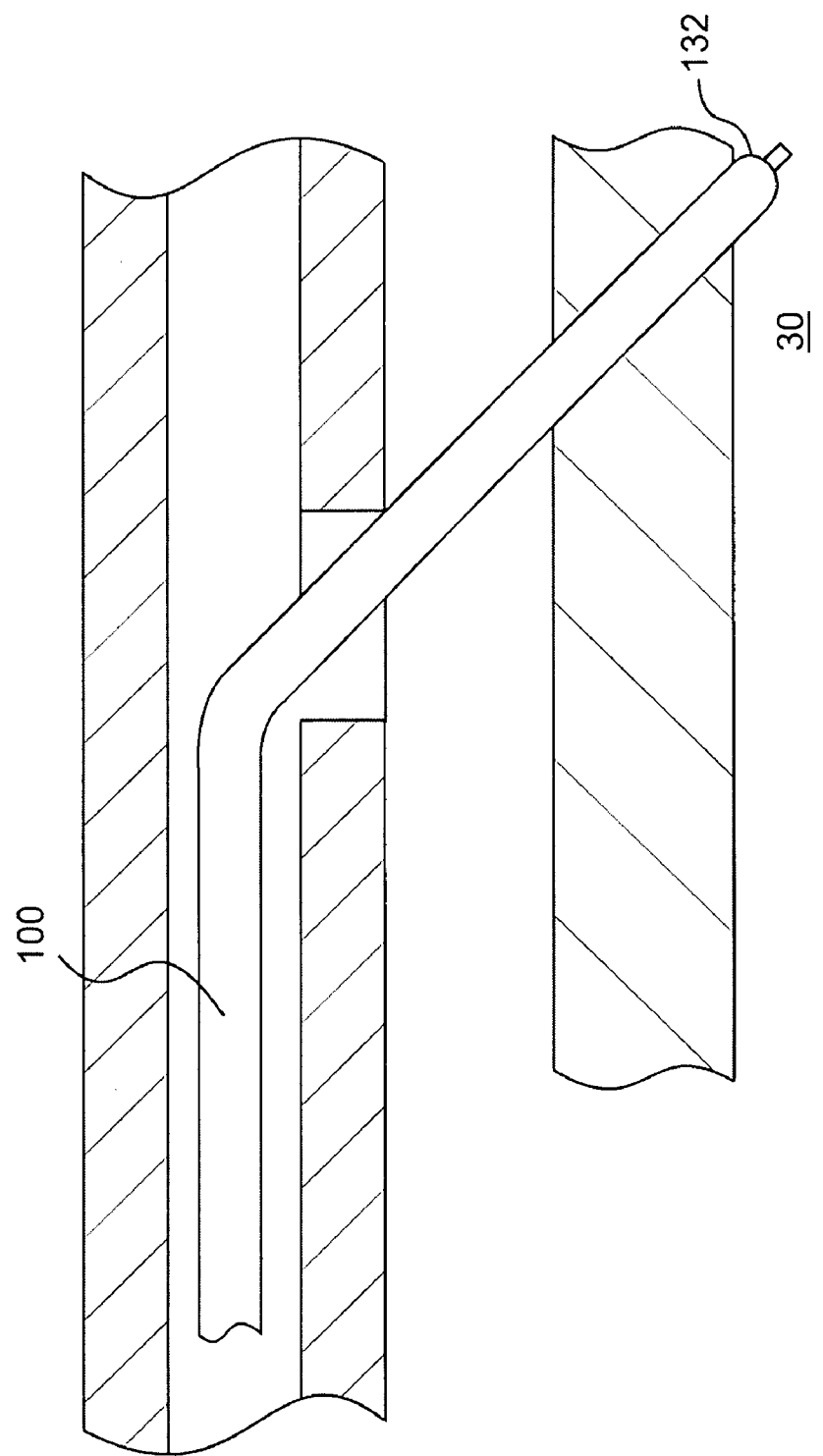
FIG. 15 is still another enlarged partial cross-sectional view showing a portion of the re-entry device shown in the previous figure. In the embodiment of FIG. 15, the re-entry device has been advanced so that the distal end of the re-entry device is disposed in the true lumen of an artery.

FIG. 15 is an enlarged partial cross-sectional view showing a portion of re-entry device 100. In the embodiment of FIG. 15, re-entry device 100 has been advanced so that distal end 132 of re-entry device 100 is disposed in true lumen 30.

Figure 16:
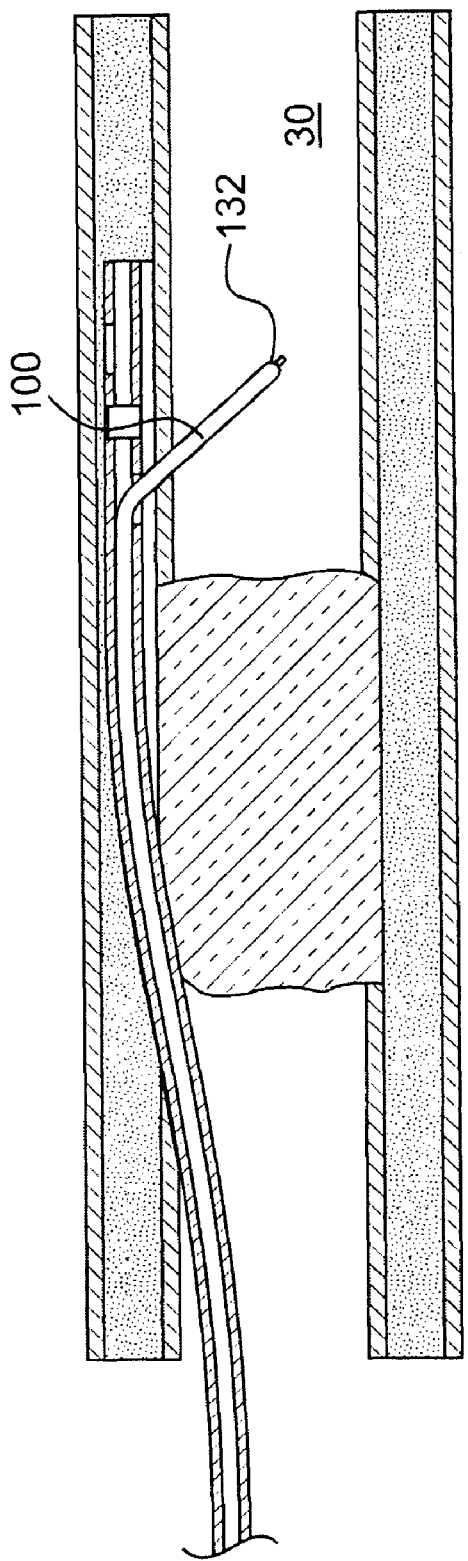
FIG. 16 is a partial cross-sectional view of the re-entry device shown in the previous figure.

FIG. 16 is a partial cross-sectional view of re-entry device 100 shown in the previous figure. FIG. 16 has a different scale than the previous figure so that more of the surrounding context is visible in FIG. 16. In FIG. 16, distal end 132 of re-entry device 100 can be seen residing in true lumen 30.

Figure 17:
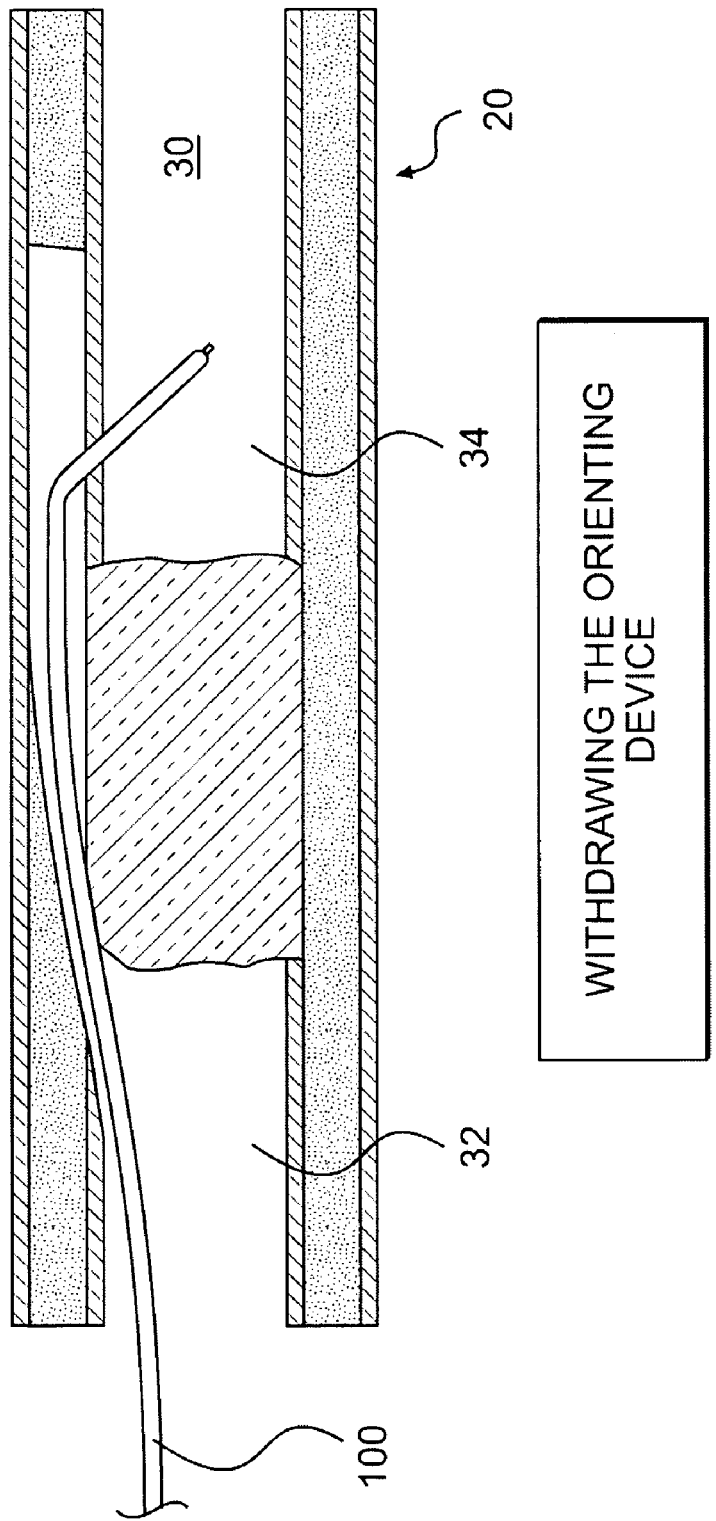
FIG. 17 is an additional view of the artery shown in the previous figure. In the embodiment of FIG. 17, an orienting device has been withdrawn leaving a re-entry device in the position shown in FIG. 17.

FIG. 17 is an additional view of artery 20 shown in the previous figure. In the embodiment of FIG. 17, orienting device 106 has been withdrawn leaving re-entry device 100 in the position shown in FIG. 17. Devices such as balloon angioplasty catheters and atherectomy catheters may be advanced over re-entry device 100. In this way, these devices may be used in conjunction with re-entry device 100 to establish a blood flow path between proximal segment 32 of true lumen 30 and distal segment 34 of true lumen 30. This path allows blood to flow around occlusion 36.

Figure 18:
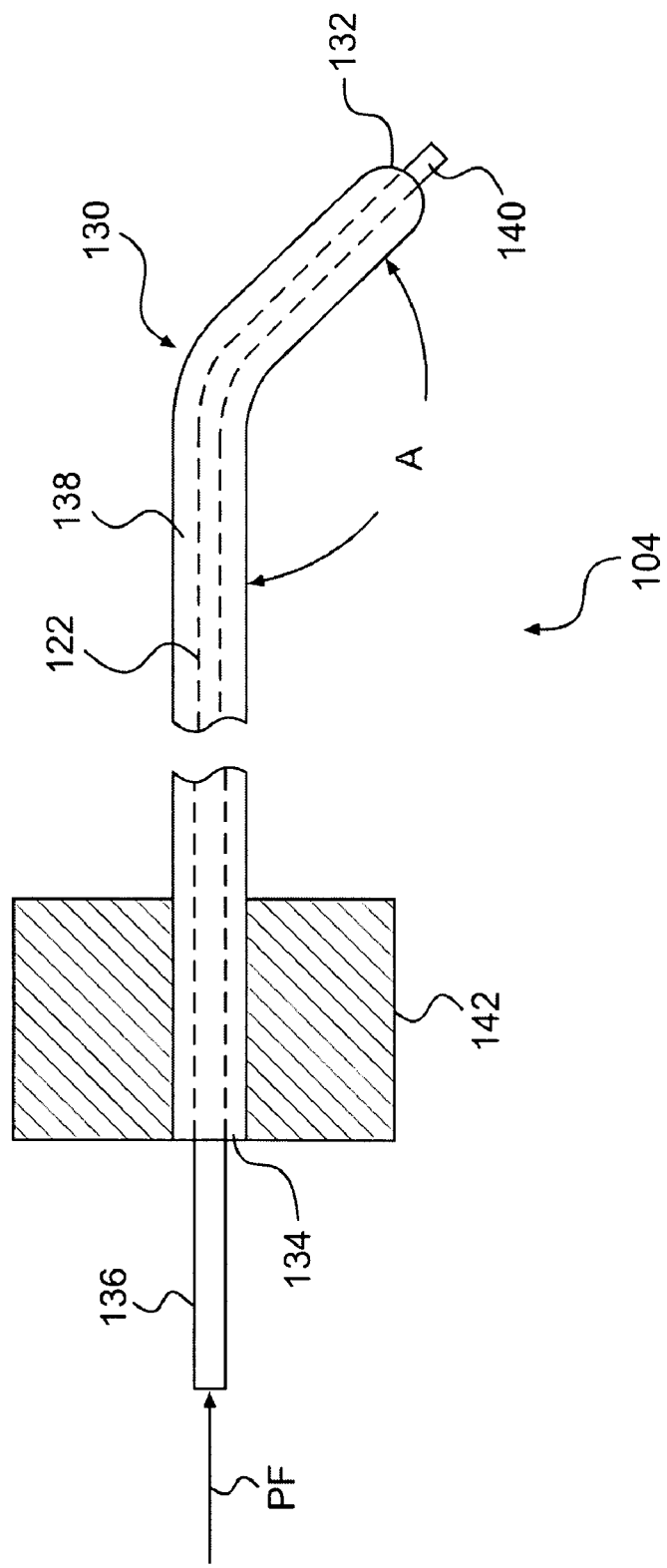
FIG. 18 is a plan view of a crossing device in accordance with the present description. In the embodiment of FIG. 19, a penetrator of the crossing device is assuming a deployed position.

FIG. 18 is a plan view of a re-entry device 100 in accordance with the present description. Crossing device 104 includes an elongate body 138 having a distal end 132 and a proximal end 134. In the embodiment of FIG. 18, a core 136 extends into a lumen 122 defined by body 138. In some useful embodiments, core 136 is free to advance and retract relative to body 138. When core 136 is moved relative to body 138, penetrator 140 can be caused to selectively assume the retracted position and/or the deployed position. In FIG. 18, penetrator 140 is shown in the deployed position.

In the embodiment of FIG. 18, an actuating fixture 142 is fixed to body 138 near proximal end 134. Also in FIG. 18, a pushing force is shown acting on a proximal portion of core 136. This pushing force is represented by an arrow PF in FIG. 18. Actuating fixture 142 may be used when creating relative motion between core 136 and body 138. Actuating fixture 142 may be held to hold body 138 relatively stationary and pushing/pulling forces may be applied to core 136 to move core 136 relative to body 138. In FIG. 18, body 138 of re-entry device 100 is shown being bent at an angle A. Accordingly, it can be said that re-entry device 100 includes a bend 130. In some useful embodiments of re-entry device 100, angle A is between about 120 degrees and about 150 degrees.

Figure 19:
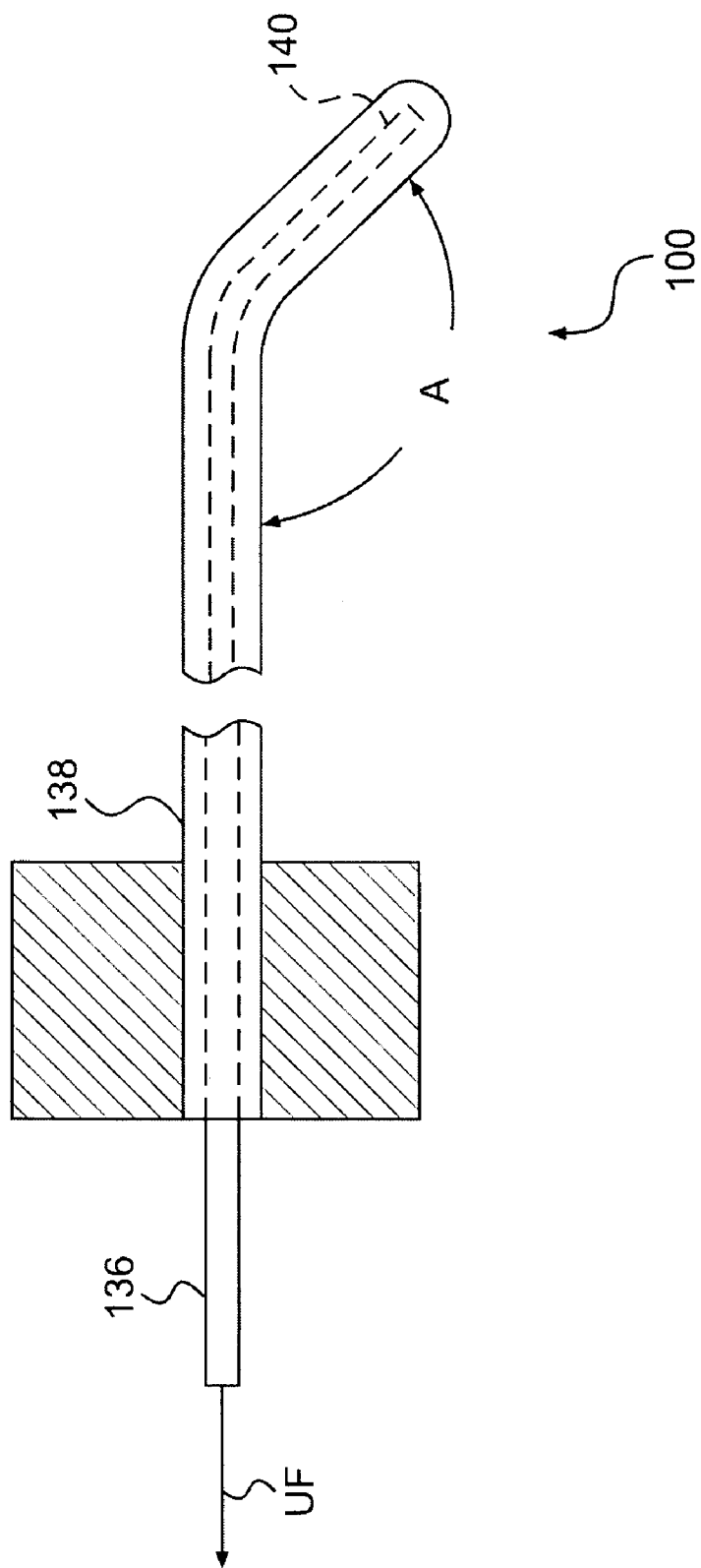
FIG. 19 is an additional plan view of the re-entry device shown in the previous figure. In the embodiment of FIG. 19, a penetrator of the crossing device is assuming a retracted position.

FIG. 19 is an additional plan view of re-entry device 100 shown in the previous figure. In the embodiment of FIG. 19, penetrator 140 is assuming a retracted position. A pulling force applied to core 136 while holding actuating fixture 142 relatively stationary may cause penetrator 140 to assume the retracted position.

With reference to the figures, it will be appreciated that when penetrator 140 is in the retracted position, the distal portion of re-entry device 100 has a less traumatic shape than when penetrator 140 is in the deployed position. Conversely, when penetrator 140 is in the deployed position, the distal portion of re-entry device 100 has a more traumatic shape than when penetrator 140 is in the retracted position.

The position of core 136 may be changed relative to body 138 by apply pushing and/or pulling forces on core 136 and body 138. In FIG. 19, a pulling force is represented with an arrow UF. A physician may utilize this mechanism to selectively alter the overall shape of a distal portion of re-entry device 100. Changes in the shape of the distal portion of re-entry device 100 may assist in re-entry through the intima.

Figure 20:
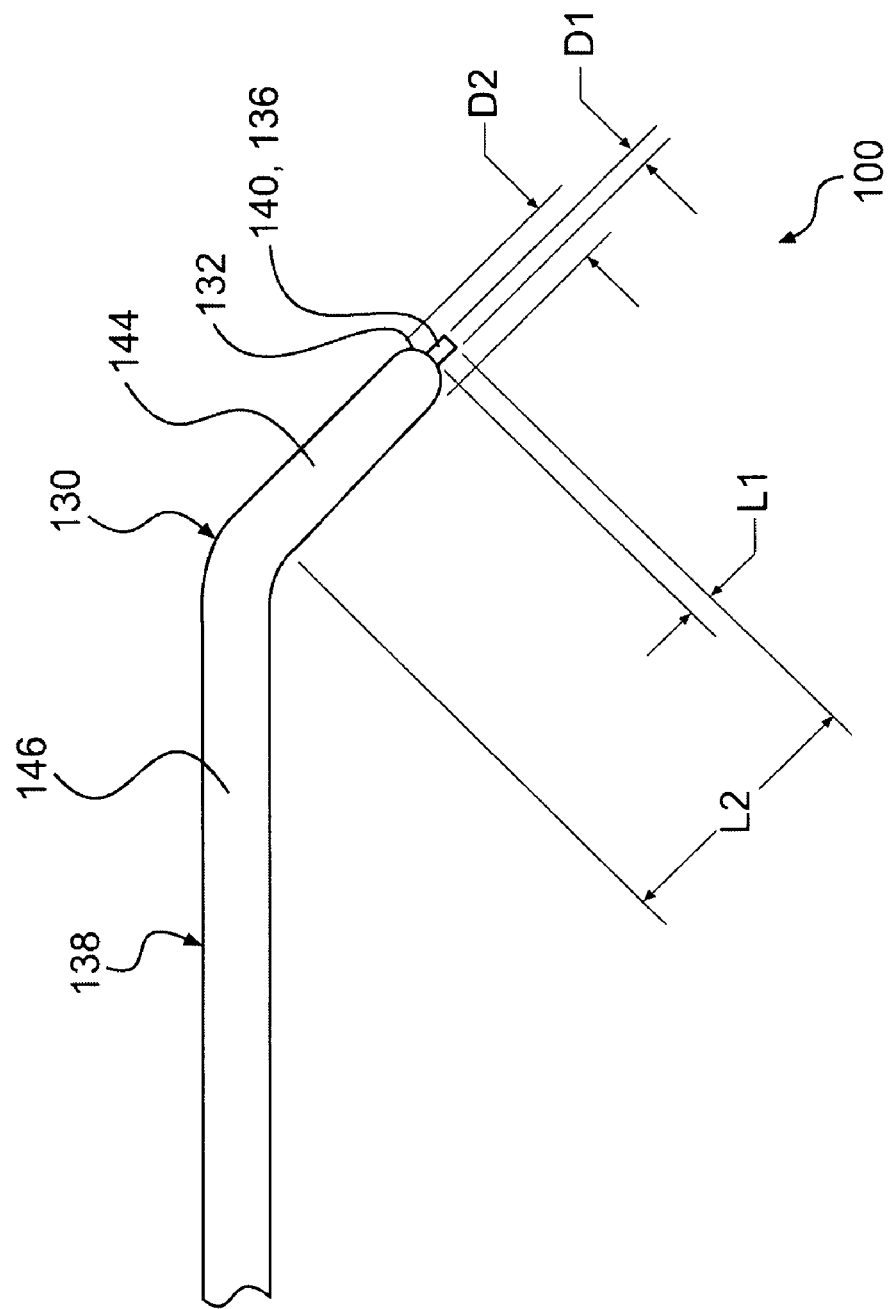
FIG. 20 is a plan view of an exemplary re-entry device. Selected dimensions of the exemplary re-entry device are illustrated in FIG. 20.

FIG. 20 is a plan view of a re-entry device 100 illustrating selected dimensions of re-entry device 100. In the embodiment of FIG. 20, a penetrator 140 of core 136 extends beyond a distal end 132 of body 138 by a distance L1. In the embodiment of FIG. 20, penetrator 140 has a diameter D1 and body 138 has a diameter D2. With reference to FIG. 20, it will be appreciated that diameter D2 of body 138 is greater than diameter D1 of penetrator 140.

With reference to FIG. 20, it will be appreciated that body 138 of re-entry device 100 includes a bend 130 near its distal end 132. Body 138 has a distal leg 144 disposed distally of bend 130 and a proximal leg 146 disposed proximally of bend 130. As shown in FIG. 20, distal leg 144 has a length of L2. With reference to FIG. 20, it will be appreciated that length L2 is greater than distance L1.

In some useful embodiments, diameter D1 of penetrator 140 is between about 0.0020 inches and about 0.0055 inches.

In some useful embodiments, diameter D2 of body 138 is between about 0.008 inches and about 0.015 inches.

In some useful embodiments, length L1 of penetrator 140 is between about 0.003 inches and about 0.012 inches.

In some useful embodiments, length L2 of distal leg 144 is between about 0.040 inches and about 0.080 inches.

Figure 21:
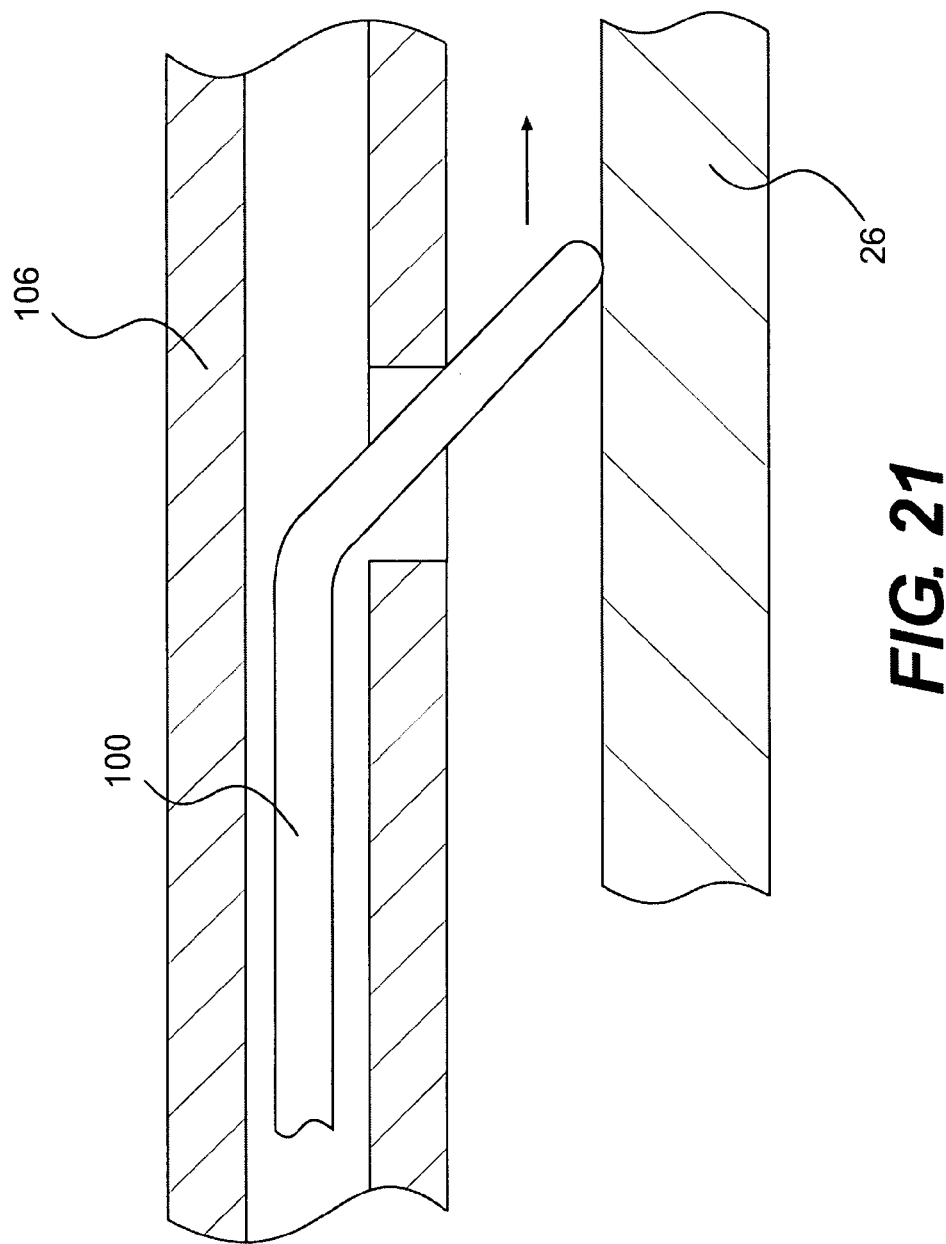
FIG. 21 and FIG. 22 illustrate a method in which a re-entry device has been advanced while a core is in a retracted position. These figures show that the re-entry device has not penetrated intima. Instead, the re-entry device has been advanced between the intima and the exterior of the orienting device.
Figure 22:
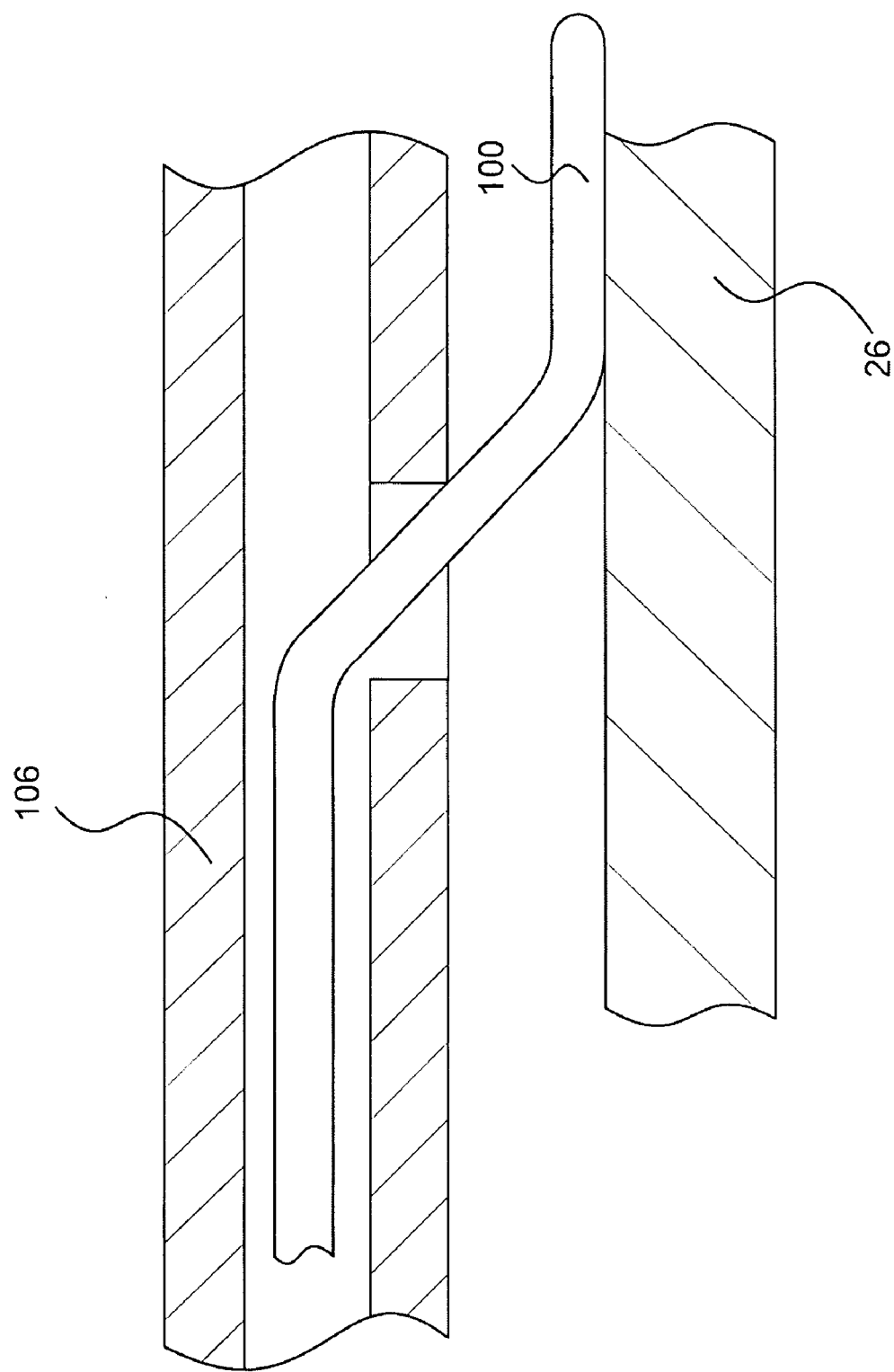

FIG. 21 and FIG. 22 illustrate a method in which re-entry device 100 has been advanced while core 136 is in a retracted position. With reference to the figures, it will be appreciated that re-entry device 100 has not penetrated intima 26. Instead, re-entry device has been advanced between intima 26 and the exterior of orienting device 106.

Figure 23B:
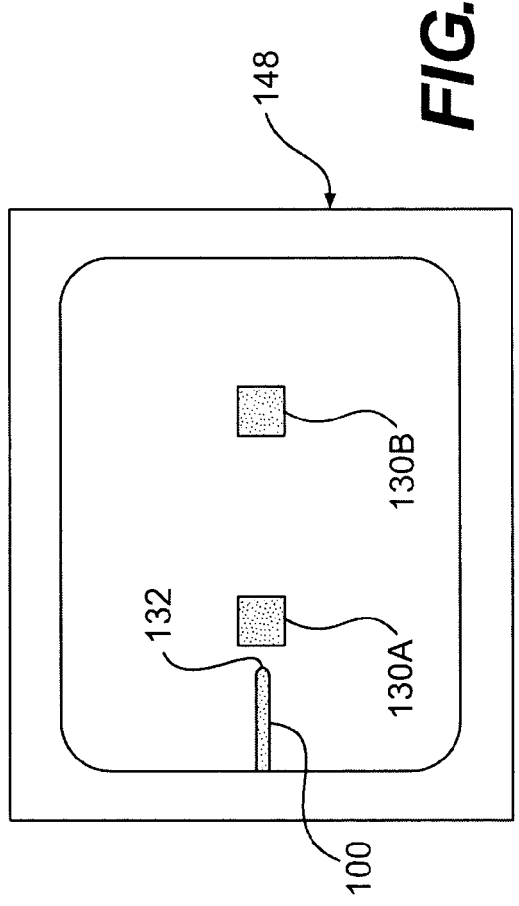
FIG. 23B is a representation of a fluoroscopic display. The radiopaque marker of the orienting device shown in the previous figure is visible in this fluoroscopic display. A radiopaque re-entry device is also visible in this display.
Figure 23A:
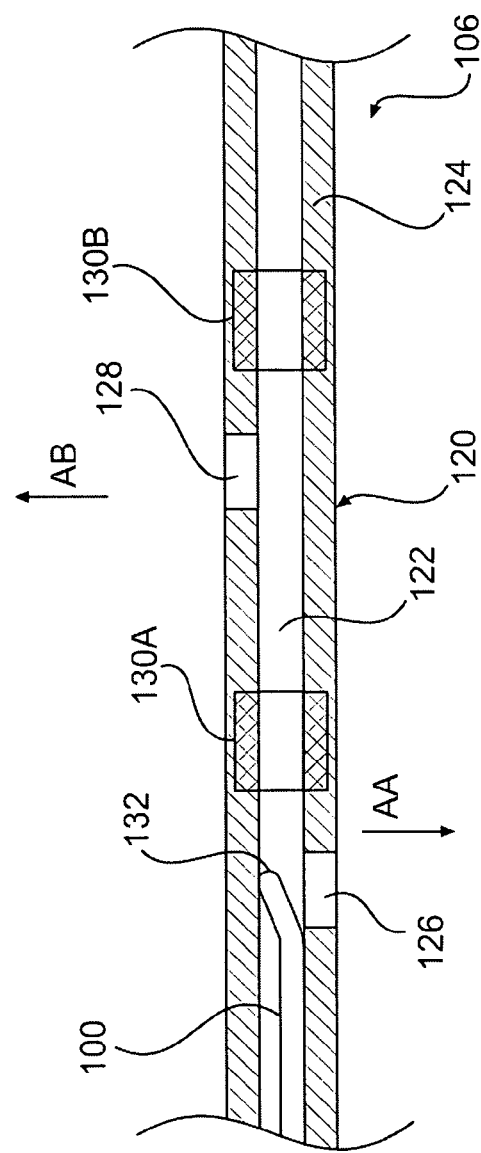
FIG. 23A is a cross-sectional view of an orienting device including a radiopaque marker.

FIG. 23A is a cross-sectional view of an orienting device 106. Orienting device 106 includes a shaft 120 comprising a wall 124 defining a lumen 122. Wall 124 defines a first aperture 126 and a second aperture 128 that are both in fluid communication with lumen 122. In the embodiment of FIG.

23A, first aperture 126 extends away from lumen 122 in a first direction that is represented by a first arrow AA in FIG. 23A. Second aperture 128 extends away from lumen 122 in a second direction that is represented by a second arrow AB in FIG. 23A. In FIG. 23A, first arrow AA and second arrow AB extend in generally opposite directions. Accordingly, the first direction is about 180 degrees from the second direction.

In the embodiment of FIG. 23A, first aperture 126 and second aperture 128 are longitudinally separated from one another. Orienting device 106 includes a first radiopaque marker 130A that is located between first aperture 126 and second aperture 128. A second radiopaque marker 130B of orienting device 106 is located distally of second aperture 128.

A re-entry device 100 is disposed in lumen 122 of orienting device 106. In the embodiment of FIG. 25A, first radiopaque marker 130A, second radiopaque marker 130B and re-entry device 100 comprise radiopaque materials. Because of the radiopaque nature of their materials of construction, first radiopaque marker 130A, second radiopaque marker 130B, and re-entry device 100 will all be visible on a fluoroscopic display during a fluoroscopic procedure.

FIG. 23B is a representation of a fluoroscopic display 148. First radiopaque marker 130A, second radiopaque marker 130B, and re-entry device 100 are visible in fluoroscopic display 148. In the embodiment of FIG. 23B, distal end 132 of re-entry device 100 is located slightly proximal of first radiopaque marker 130A. Accordingly, re-entry device 100 is seen extending across fluoroscopic display 148 and ending just short of first radiopaque marker 130A. When a physician views display 148 shown in FIG. 23B, the physician may infer that distal end 132 is proximate first aperture 126 of orienting device 106. After determining that distal end 132 of re-entry device 100 is in this location, the physician can rotate re-entry device 100 until distal end 132 enters into first aperture 126.

FIG. 24 is a plan view including orienting device 106 shown in the previous figure. In FIG. 24, a distal portion of re-entry device 100 can be seen extending through first aperture 126. First aperture 126 and second aperture 128 both fluidly communicate with lumen 122 of orienting device 106. Orienting device 106 includes a first radiopaque marker 130A that is located between first aperture 126 and second aperture 128. A second radiopaque marker 130B of orienting device 106 is located distally of second aperture 128.

Orienting device 106 comprises an elongate shaft 120, a first orienting element 150, and second orienting element (not visible in FIG. 24). First orienting element 150 comprises a first balloon 152 and second orienting element comprises a second balloon. When these balloons are inflated between the adventitia and the intima of a blood vessel, orienting device 106 will orient itself within the blood vessel so that either first aperture 126 or second aperture 128 will open toward a true lumen of the artery. The physician may select the aperture opening toward the true lumen using methods described herein. The physician may then use methods in accordance with this disclosure to insert distal end 132 of re-entry device 100 through the selected aperture.

FIG. 25A is a cross-sectional view of an orienting device 106. Orienting device 106 includes a shaft 120 comprising a wall 124 defining a lumen 122. In the embodiment of FIG. 25, a re-entry device 100 is disposed in lumen 122. Wall 124 defines a first aperture 126 and a second aperture 128 that are both in fluid communication with lumen 122.

In the embodiment of FIG. 25A, first aperture 126 and second aperture 128 are longitudinally separated from one another. Orienting device 106 includes a first radiopaque marker 130A that is located between first aperture 126 and second aperture 128. Orienting device 106 also comprises a second radiopaque marker 130B that is located distally of second aperture 128. With reference to FIG. 25A, it will be appreciated that first radiopaque marker 130A and second radiopaque maker 130B are both surrounded by wall 124 of shaft 120.

In the embodiment of FIG. 25A, first radiopaque marker 130A, second radiopaque marker 130B and re-entry device 100 comprise radiopaque materials. Because of the radiopaque nature of their materials of construction, first radiopaque marker 130A, second radiopaque marker 130B, and re-entry device 100 will all be visible on a fluoroscopic display during a fluoroscopic procedure.

FIG. 25B is a representation of a fluoroscopic display 148. First radiopaque marker 130A, second radiopaque marker 130B, and re-entry device 100 are visible in fluoroscopic display 148. In the embodiment of FIG. 25B, distal end 132 of re-entry device 100 is located slightly proximal of second radiopaque marker 130B. Accordingly, re-entry device 100 is seen extending across fluoroscopic display 148 and ending just short of second radiopaque marker 130B. When a physician views display 148 shown in FIG. 25B, the physician may infer that distal end 132 is proximate second aperture 126 of orienting device 106. After determining that distal end 132 of re-entry device 100 is in this location, the physician can rotate re-entry device 100 until distal end 132 enters into second aperture 126.

Figure 26:
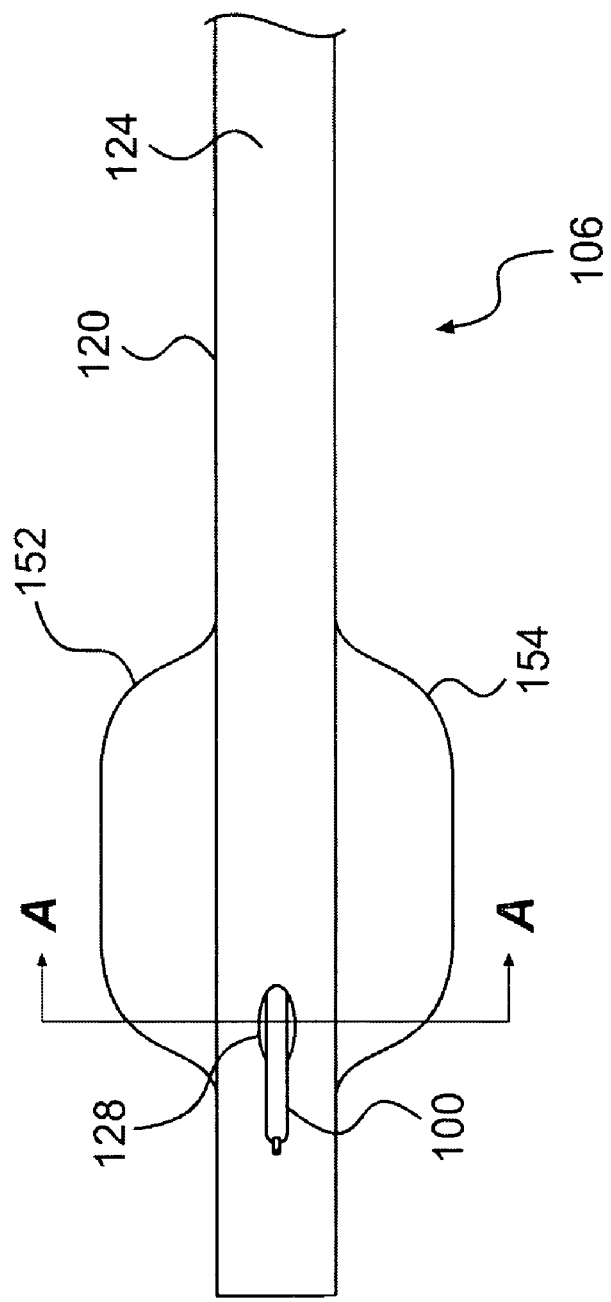
FIG. 26 is a plan view including the orienting device shown in the previous figure. A first balloon and a second balloon of the orienting device are visible in FIG. 26.

FIG. 26 is a plan view including orienting device 106 shown in the previous figure. Orienting device 106 comprises an elongate shaft 120, a first balloon 152, and a second balloon 154. In the embodiment of FIG. 26, first balloon 152 and second balloon 154 are both formed from extruded portions of an outer wall 124 of elongate shaft 120. Outer wall 124 defines a second aperture 128. In FIG. 26, a re-entry device 100 is shown extending through second aperture 128.

Figure 27:
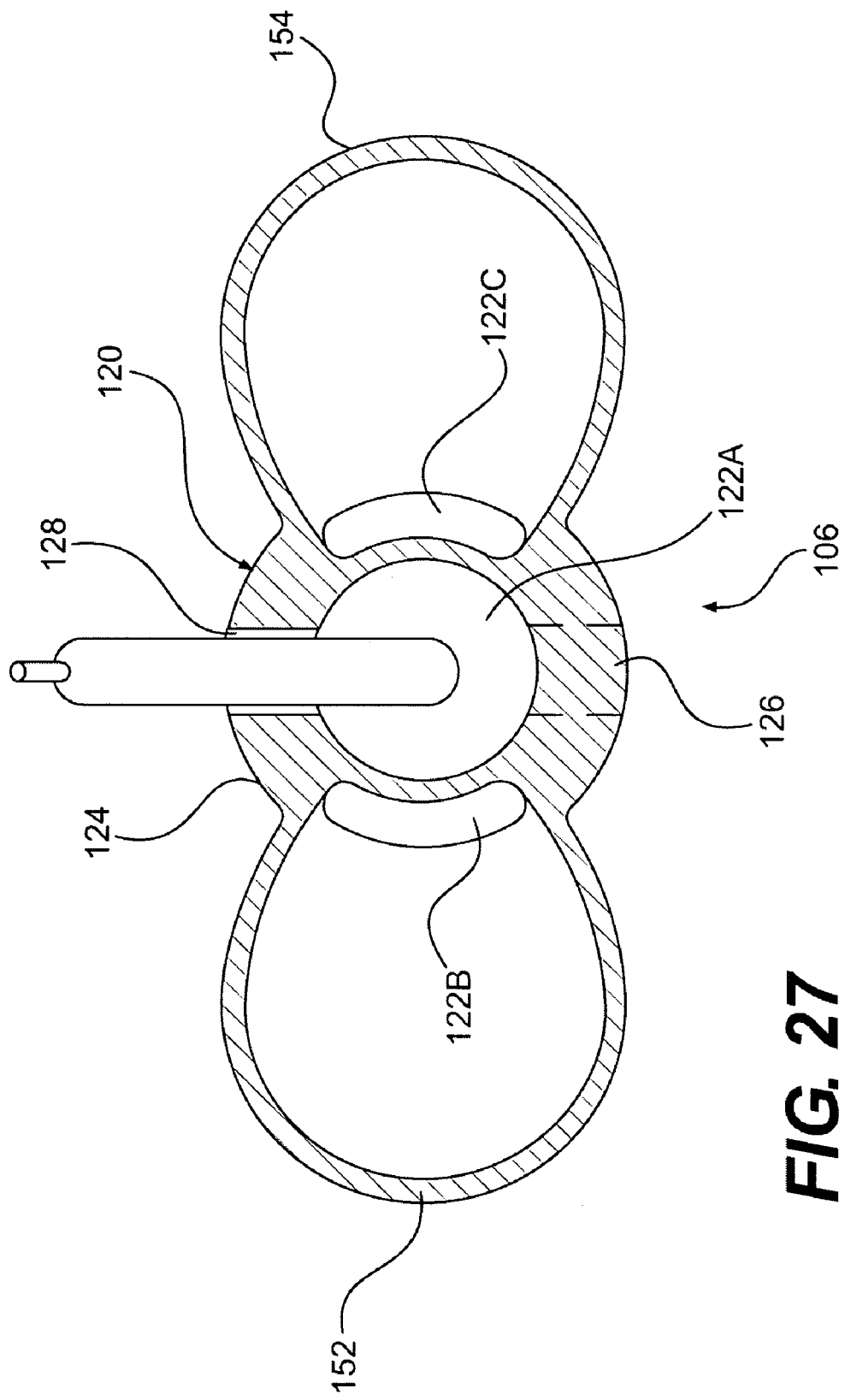
FIG. 27 is a cross sectional view of the orienting device shown in the previous figure. A cut of the cross-sectional view is taken along line A-A shown in FIG. 27.

FIG. 27 is a cross sectional view of orienting device 106 taken along line A-A shown in FIG. 26. With reference to FIG. 27, it will be appreciated that elongate shaft 120 defines a lumen 122A, a first planetary lumen 122B, and a second planetary lumen 122C. The planetary lumens are defined in part by an outer wall 124 of elongate shaft 120. Outer wall 124 defines a first aperture 126 and a second aperture 128.

In the embodiment of FIG. 27, a first balloon 152 is formed of an extruded portion of outer wall 124 of elongate shaft 120. First balloon 152 defines an interior that is in fluid communication with first planetary lumen 122B. In the embodiment of FIG. 27, first balloon 152 and elongate shaft 120 are monolithic. As shown in FIG. 27, first balloon 152 and outer wall 124 of elongate shaft 120 are seamlessly formed from a single piece of material. With reference to FIG. 27, it will be appreciated that second balloon 154 defines an interior that is in fluid communication with second planetary lumen 122C. In the embodiment of FIG. 27, second balloon 154 comprises an extruded portion of outer wall 124 of elongate shaft 120.

As shown in FIG. 27, second balloon 154 and elongate shaft 120 are seamlessly formed from a single piece of material. Second balloon 154 may be formed, for example, by extruding a portion of outer wall 124. In some useful embodiments, elongate shaft 120 comprises a thermoplastic material. When this is the case, elongate shaft 120 may be formed, for example, using an extrusion process. Also when this is the case, first balloon 152 and second balloon 154 may be formed by further extruding outer wall 124 of elongate shaft 120.

Figure 28:
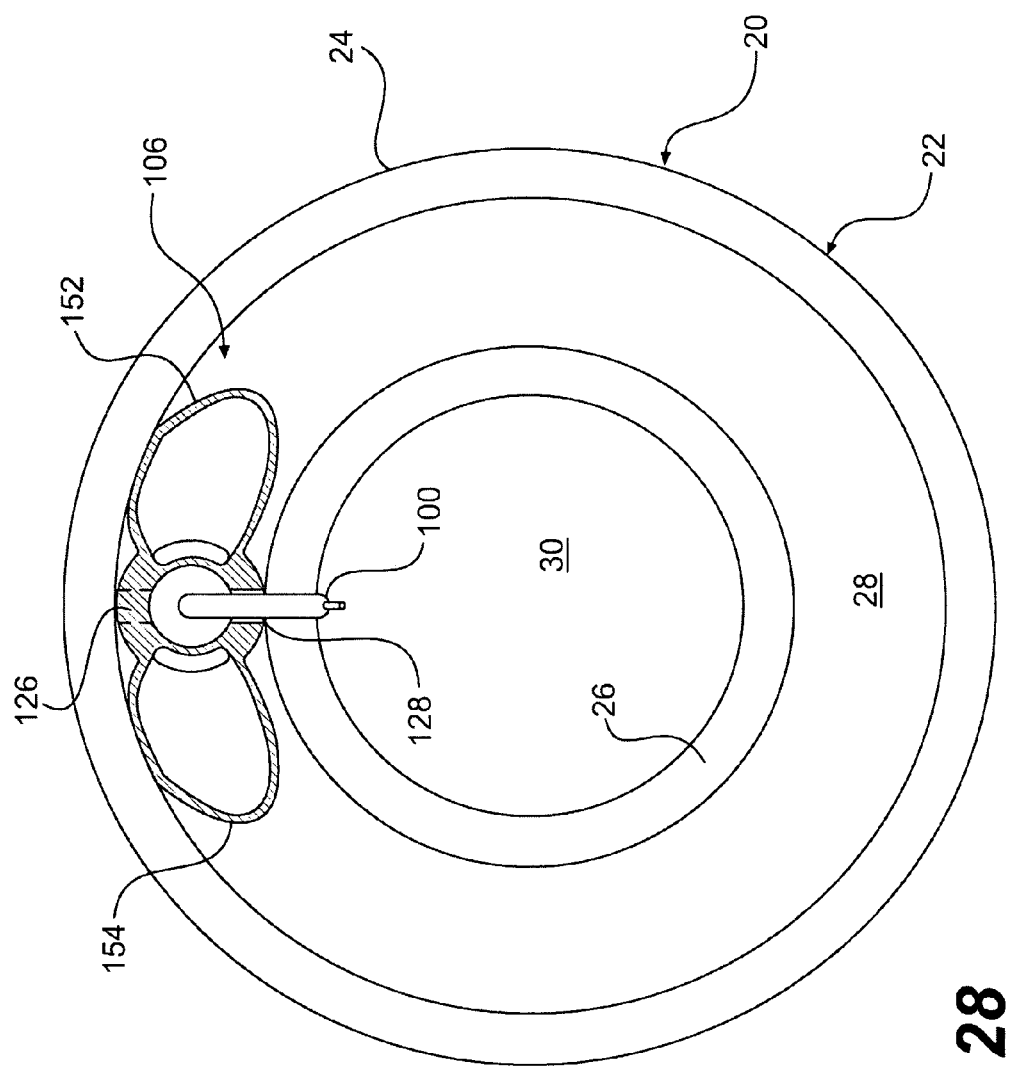
FIG. 28 is a cross-sectional view of an artery with a wall having three layers. The outermost layer of the wall is the adventitia and the innermost layer is the intima.

FIG. 28 is a cross-sectional view of an artery 20 having a wall 22. In FIG. 28, wall 22 of artery 20 is shown having three layers. The outermost layer of wall 22 is the adventitia 24 and the innermost layer of wall 22 is the intima 26. The tissues extending between intima 26 and adventitia 24 may be collectively referred to as the media 28. For purposes of illustration, intima 26, media 28 and adventitia 24 are each shown as a single homogenous layer in FIG. 28. In the human body, however, the intima and the media each comprise a number of sub-layers. The transition between the external most portion of the intima and the internal most portion of the media is sometimes referred to as the subintimal space. Intima 26 defines a true lumen 30 of artery 20.

In FIG. 28, orienting device 106 is shown disposed between adventitia 24 and intima 26 of artery 20. Orienting device 106 may be used to direct a re-entry device 100 toward true lumen 30 of artery 20 as shown in FIG. 28. The first aperture 126 and second aperture 128 are generally oriented at a right angle to a plane defined by first balloon 152 and second balloon 154. With this arrangement, each aperture is either directed toward true lumen 30 of artery 20 or 180 degrees away from true lumen 30 when first balloon 152 and second balloon 154 are inflated. In this way, orienting device 106 reduces the number of directions an aperture may be facing from 360 degrees of freedom to two degrees of freedom, 180 degrees apart.

Figure 29:
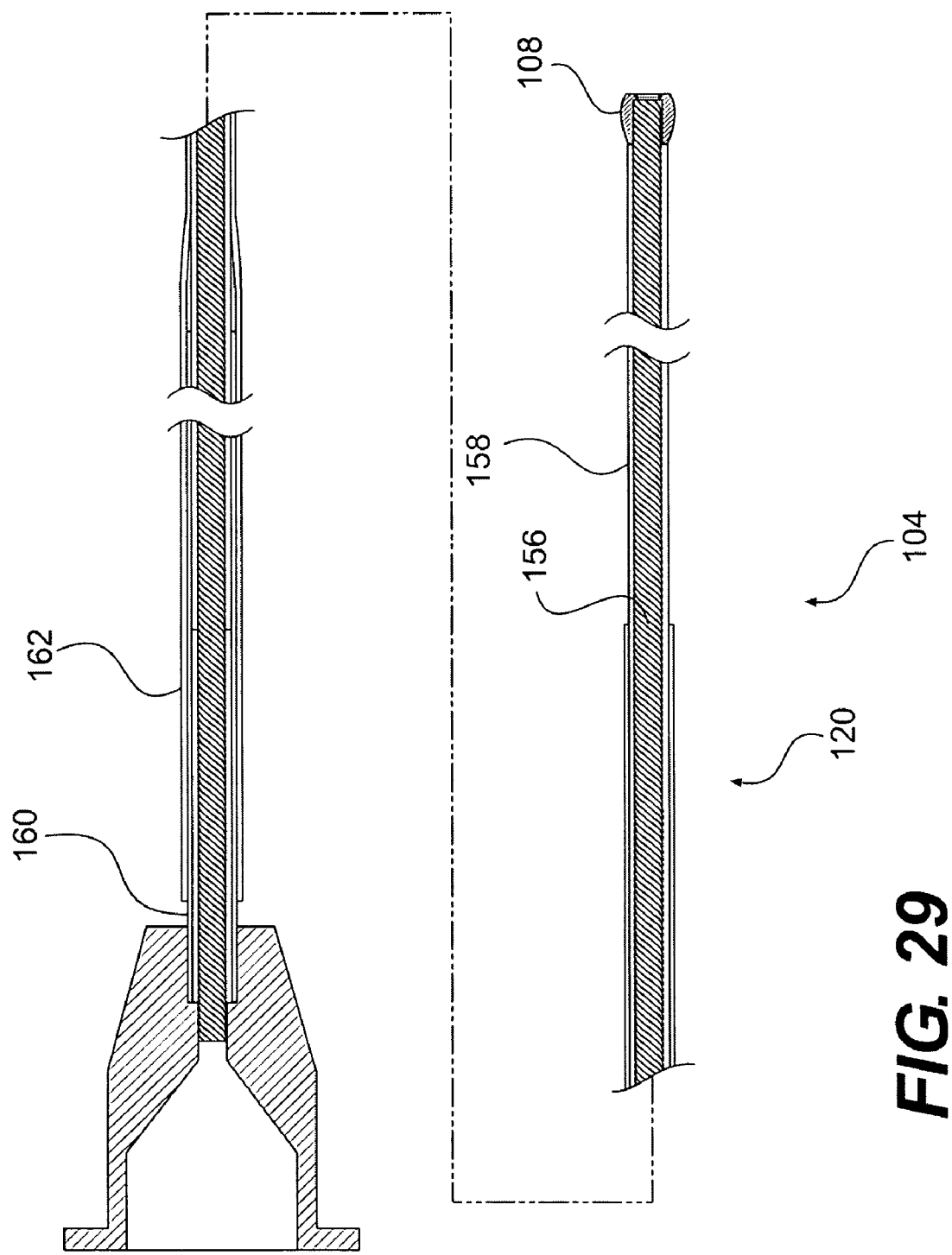
FIG. 29 is a partial cross-sectional view of an exemplary crossing device comprising a tip that is fixed to a distal end of a shaft.

FIG. 29 is a partial cross-sectional view of an exemplary crossing device 104. Crossing device 104 of FIG. 29 comprises a tip 108 that is fixed to a distal end of a shaft 120. In the exemplary embodiment of FIG. 29, shaft 120 comprises a coil 156, a sleeve 158, a tubular body 160, and a sheath 162.

Tip 108 is fixed to a distal portion of coil 156. Coil 156 comprises a plurality of filars that are wound in a generally helical shape. In some useful embodiments of crossing device 104, coil 156 comprises eight, nine or ten filars wound into the shape illustrated in FIG. 29. Crossing device 104 includes a sleeve 158 that is disposed about a portion of coil 156. Sleeve 158 may comprise, for example, PET shrink tubing, i.e. polyethylene terephthalate.

Sleeve 158 and coil 156 both extend into a lumen defined by a tubular body 160. Tubular body 160 may comprise, for example hypodermic tubing formed of Nitnol, i.e. nickel titanium. With reference to FIG. 29, it will be appreciated that a proximal portion of sleeve 158 is disposed between tubular body 160 and coil 156. In some embodiments of crossing device 104, a distal portion of tubular body 160 defines a helical cut. This helical cut may be formed, for example, using a laser cutting process. The helical cut may be shaped and dimensioned to provide an advantageous transition in lateral stiffness proximate the distal end of tubular body 160.

A proximal portion of coil 156 extends proximally beyond the distal end of tubular body 160. A hub is fixed to a proximal portion of coil 156 and a proximal portion of tubular body 160. The hub may comprise, for example, a luer fitting. A sheath 162 is disposed about a portion of tubular body 160 and a portion of sleeve 158. In some embodiments of crossing device 104, sheath 162 comprises HYTREL, a thermoplastic elastomer.

With reference to FIG. 29, it will be appreciated that tubular body 160, coil 156, sleeve 158, and sheath 162 each have a proximal end and a distal end. The proximal end of outer sleeve 158 is disposed between the proximal end of tubular body 160 and the proximal end of sleeve 158. The distal end of sleeve 158 is positioned proximate tip 108 that is fixed to the distal end of coil 156. The distal end of sheath 162 is located between the distal end of tubular body 160 and the distal end of sleeve 158. With reference to FIG. 29, it will be appreciated that sheath 162 overlays the distal end of tubular body 160.

With reference to FIG. 29, it will be appreciate that tip 108 has a generally rounded shape. The generally rounded shape of tip 108 may reduce the likelihood that crossing device 104 will penetrate the adventitia of an artery. Tip 108 may be formed from a suitable metallic material including but not limited to stainless steel, silver solder, and braze. Tip 108 may also be formed from suitable polymeric materials or adhesives including but not limited to polycarbonate, polyethylene and epoxy. In some embodiments of crossing device 104, the outer surface of tip 108 comprises a generally non-abrasive surface. For example, the outer surface of tip 108 may have a surface roughness of about 25 micrometers or less. A tip member having a relatively smooth outer surface may reduce the likelihood that the tip member will abrade the adventitia of an artery.

Figure 30:
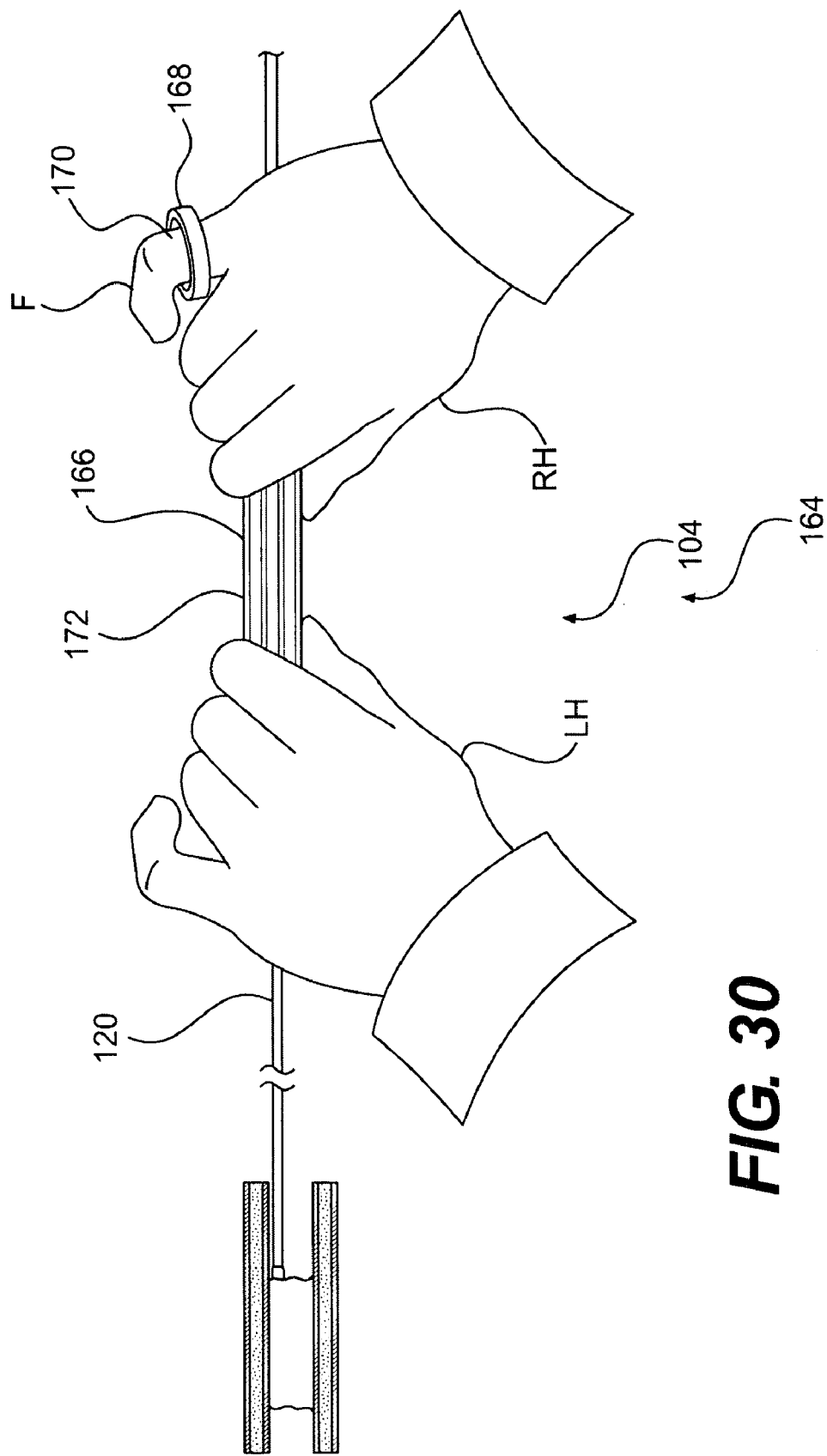
FIG. 30 is a plan view showing an assembly including the crossing device shown in the previous figure. In the embodiment of FIG. 30, a drive assembly is coupled to the shaft of the crossing device.

FIG. 30 is a plan view showing an assembly 164 including crossing device 104 shown in the previous figure. In the embodiment of FIG. 30, a drive assembly 166 is coupled to crossing device 104. In FIG. 30, drive assembly 166 is shown disposed about a proximal portion of shaft 120 of crossing device 104. Drive assembly 166 comprises a handle body 172 and an anchor 168.

As shown in FIG. 30, handle body 172 of drive assembly 166 is long enough to receive the thumb and forefingers of a right hand RH and a left hand LH. Anchor 168 of drive assembly 166 defines a hole 170. With reference to FIG. 30, it will be appreciated that a finger F of right hand RH is extending through hole 170 in anchor 168. Left hand LH and right hand RH may rotate handle body 172 of drive assembly 166. When this is the case, finger F extending through anchor 168 prevents anchor 168 from rotating while handle body 172 rotates.

In FIG. 30, a distal portion of handle body 172 is positioned between the thumb and forefinger of a left hand LH. A proximal portion of handle body 172 is disposed between the thumb and forefinger of a right hand RH. In some useful methods, crossing device 104 is rotated and axially advanced simultaneously. Rotation of crossing device 104 can be achieved by rolling handle body 172 between the thumb and forefinger one hand. Two hands can also be used as shown in FIG. 30. Rotating crossing device 104 assures that the coefficient of friction at the interface between the crossing device and the surrounding tissue will be a kinetic coefficient of friction and not a static coefficient of friction.

Figure 31:
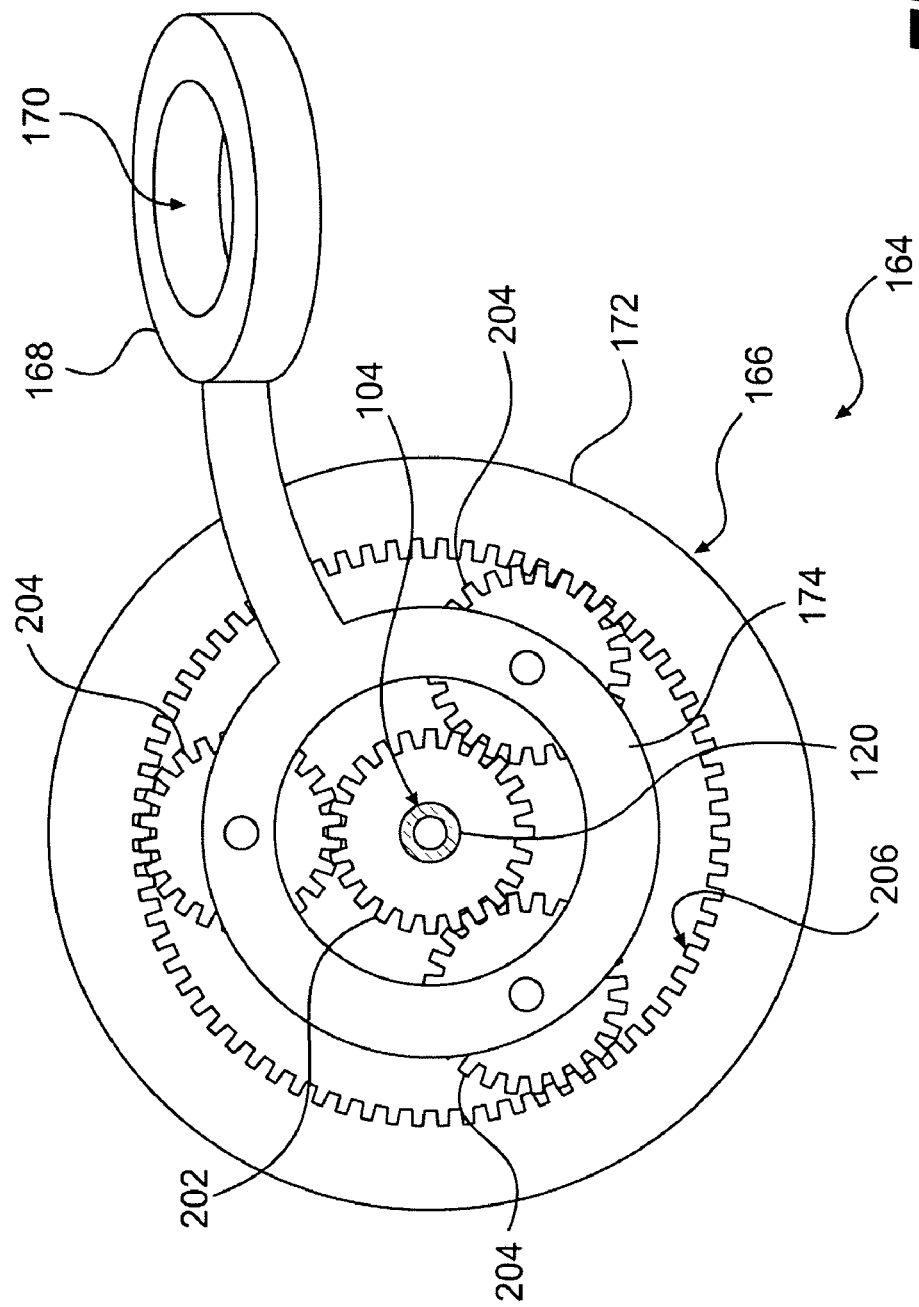
FIG. 31 is a cross-sectional view of the assembly shown in the previous figure. The assembly includes a drive assembly comprising a central gear, an internal gear and a plurality of planetary gears. These gears form a gear train that provides a mechanical advantage.

FIG. 31 is a cross-sectional view of assembly 164 shown in the previous figure. Assembly 164 includes a drive assembly 166 and a crossing device 104. With reference to FIG. 31, it will be appreciated that drive assembly 166 includes a central gear 202 that is fixed to shaft 120 of crossing device 104. Drive assembly 166 also includes a handle body 172. An internal gear 206 is fixed to handle body 172.

A plurality of planetary gears 204 are disposed between central gear 202. A ring 174 maintains the spacing between adjacent pairs planetary gears 204. Anchor 168 is fixed to ring 174. Anchor 168 defines a hole 170. Central gear 202, planetary gears 204, and internal gear 206 together form a gear train providing a mechanical advantage. Due to this mechanical advantage, a single rotation of handle body 172 results in many rotations of shaft 120 of crossing device 104.

In some useful methods in accordance with the present disclosure, crossing device 104 is rotated at a rotational speed of between about 2 revolutions per minute and about 200 revolutions per minute. In some particularly useful methods in accordance with the present disclosure, crossing device 104 is rotated at a rotational speed of between about 50 revolutions per minute and about 150 revolutions per minute.

Crossing device 104 may be rotated by hand as depicted in the previous figure. It is also contemplated that a mechanical device (e.g., an electric motor) may be used to rotate crossing device 104.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of facilitating treatment via a vascular wall defining a vascular lumen containing an occlusion therein, the method comprising:
    positioning a distal portion of a first intravascular device in the vascular wall, the first intravascular device including a first aperture, a second aperture, a first radiopaque marker, and a second radiopaque marker, the first aperture being longitudinally offset from the second aperture with the first aperture located proximal the second aperture, the first radiopaque marker being located between the first aperture and the second aperture, the second radiopaque marker being located distal the second aperture;
    inserting a distal end of a reentry device, in a compressed state, in the distal portion of the first intravascular device;
    positioning the distal end of the reentry device proximal the first radiopaque marker of the first intravascular device;
    rotating the reentry device until the distal end of the reentry device, in a natural state, enters the first aperture of the first intravascular device;
    positioning the distal end of the reentry device proximal the second radiopaque marker of the first intravascular device and distal the first radiopaque marker of the first intravascular device;
    rotating the reentry device until the distal end of the reentry device, in the natural state, enters the second aperture of the first intravascular device; and
    advancing the distal end, in a natural state, through the second aperture of the first intravascular device.

2. The method of claim 1, wherein when the distal end is in the natural state, the distal end forms an angle with a body of the reentry device.

3. The method of claim 2, wherein the angle is between about 120 degrees and about 150 degrees.

4. The method of claim 1, further including directing the distal end of the reentry device towards the vascular lumen and into contact with an intimal layer of the vascular wall.

5. The method of claim 1, wherein the reentry device includes a body, the body defining a device lumen, and a core located in the device lumen that is movable relative to the device lumen.

6. The method of claim 5, further including moving a distal tip of the core of the reentry device beyond the distal end of the reentry device.

7. The method of claim 5, further comprising piercing an intimal layer of the vascular wall with the reentry device, and advancing the distal end of the reentry device into the vascular lumen.

8. The method of claim 7, wherein the core includes a penetrator, and wherein the penetrator is configured to pierce an intimal layer of the vascular wall before the distal end of the reentry device is advanced into the vascular lumen.

9. The method of claim 1, further including:
    positioning a second intravascular device in the vascular wall prior to positioning the distal portion of the first intravascular device in the vascular wall; and
    advancing a distal portion of the second intravascular device in the vascular wall beyond the occlusion.

10. The method of claim 9, further including advancing a guidewire through a lumen of the second intravascular device, and removing the second intravascular device from the vascular wall while leaving the guidewire in the vascular wall.

11. The method of claim 10, wherein positioning the distal portion of the first intravascular device in the vascular wall comprises advancing the first intravascular device over the guidewire.

12. The method of claim 11, further comprising withdrawing the guidewire from a guidewire lumen of the first intravascular device.

13. The method of claim 12, further comprising advancing at least a portion of the reentry device into the guidewire lumen of the first intravascular device.

14. The method of claim 13, further comprising removing the first intravascular device from the vascular wall while a distal portion of the reentry device is extending through an intimal portion of the vascular wall.

15. The method of claim 14, further comprising advancing a therapy catheter over the reentry device.

16. A method of facilitating treatment via a vascular wall defining a vascular lumen containing an occlusion therein, the method comprising:
    positioning a distal portion of a first intravascular device in the vascular wall;
    inserting a distal end of a reentry device in the distal portion of the first intravascular device, the reentry device including a penetrator that extends distally beyond a distal surface of a body of the reentry device;
    positioning the distal end of the reentry device proximate a first aperture of the first intravascular device;
    rotating the reentry device until the distal end of the reentry device enters the first aperture of the first intravascular device;
    positioning the distal end of the reentry device proximate a second aperture of the first intravascular device;
    rotating the reentry device until the distal end of the reentry device enters the second aperture of the first intravascular device; and
    advancing the penetrator through the second aperture of the first intravascular device.

17. The method of claim 16, further comprising contacting an intimal layer of the vascular wall with the penetrator.

18. The method of claim 17, further comprising contacting the intimal layer of the vascular wall with the distal end.

19. The method of claim 18, wherein the penetrator contacts the intimal layer of the vascular wall before the distal surface of the body of the reentry device contacts the intimal layer of the vascular wall.

20. The method of claim 16, further comprising piercing the intimal layer of the vascular wall with the penetrator.

21. The method of claim 20, further comprising piercing the intimal layer of the vascular wall with the distal end.

22. The method of claim 21, wherein the penetrator pierces the intimal layer of the vascular wall before the distal surface of the body pierces the intimal layer of the vascular wall.

23. The method of claim 16, wherein the reentry device has a core including the penetrator, the core being movable relative to the body of the reentry device, and further including moving the core relative to the body.

24. The method of claim 23, wherein moving the core relative to the body comprises moving a distal end of the core beyond the distal surface of the body.

25. The method of claim 16, wherein the penetrator is fixed relative to the body.

26. The method of claim 16, further comprising advancing the distal end of the reentry device into the vascular lumen.

27. The method of claim 16, wherein the first intravascular device includes a second aperture.

28. The method of claim 27, wherein the first aperture is located proximal the second aperture.

29. The method of claim 16, further including determining whether the distal end of the reenty device is directed toward the vascular lumen or directed away from the vascular lumen, wherein determining whether the distal end of the reentry device is directed toward the vascular lumen or directed away from the vascular lumen comprises viewing the distal end of the reentry device using fluoroscopy.

30. The method of claim 29, further comprising advancing the distal end tip of the reentry device through an intimal portion of the vascular wall if it is determined that the distal end tip of the reentry device is directed toward the vascular lumen.

31. The method of claim 29, further comprising advancing the distal end tip of the reentry device into the vascular lumen if it is determined that the distal end tip of the reentry device is directed toward the vascular lumen.

32. The method of claim 29, further comprising withdrawing the distal end tip of the reentry device into the first intravascular device if it is determined that the distal end tip of the reentry device is directed away from the vascular lumen.

33. The method of claim 16, further comprising withdrawing one of a guidewire and the reentry device from a guidewire lumen of the first intravascular device and advancing the other of the guidewire and the reentry device into the guidewire lumen of the first intravascular device.

34. The method of claim 1, further including determining whether the distal end of the reenty device is directed toward the vascular lumen or directed away from the vascular lumen, wherein determining whether the distal end of the reentry device is directed toward the vascular lumen or directed away from the vascular lumen comprises viewing the distal end of the reentry device using fluoroscopy.

35. The method of claim 1, further comprising advancing the distal end of the reentry device through an intimal portion of the vascular wall if it is determined that the distal end of the reentry device is directed toward the vascular lumen.

36. The method of claim 1, further comprising advancing the distal end of the reentry device into the vascular lumen if it is determined that the distal end of the reentry device is directed toward the vascular lumen.

37. The method of claim 1, further comprising withdrawing the distal end of the reentry device into the first intravascular device if it is determined that the distal end of the reentry device is directed away from the vascular lumen.

38. The method of claim 1, further comprising determining whether the distal end of the reentry device, advanced through the other of the first aperture and the second aperture, is directed toward the vascular lumen or directed away from the vascular lumen.

39. The method of claim 1, further comprising withdrawing one of a guidewire and the reentry device from a guidewire lumen of the first intravascular device and advancing the other of the guidewire and the reentry device into the guidewire lumen of the first intravascular device.

40. A method of facilitating treatment via a vascular wall defining a vascular lumen containing an occlusion therein, the method comprising:
  positioning a distal portion of a first intravascular device in the vascular wall;
  inserting a distal end of a reentry device in the distal portion of the first intravascular device;
  positioning the distal end of the reentry device proximate a first aperture of the first intravascular device;
  rotating the reentry device until the distal end of the reentry device enters the first aperture of the first intravascular device;
  positioning the distal end of the reentry device proximate a second aperture of the first intravascular;
  rotating the reentry device until the distal end of the reentry device enters the second aperture of the first intravascular device; and
  advancing the distal end through the second aperture of the first intravascular device.

41. The method of claim 40, wherein the distal end has a natural state such that when the distal end is in the natural state, the distal end forms an angle with a body of the reentry device.

42. The method of claim 41, wherein the angle is between about 120 degrees and about 150 degrees.

43. The method of claim 40, further including directing the distal end of the reentry device towards the vascular lumen and into contact with an intimal layer of the vascular wall.

44. The method of claim 40, wherein the reentry device includes a body, the body defining a device lumen.

45. The method of claim 44, further comprising piercing an intimal layer of the vascular wall with the reentry device, and advancing the distal end of the reentry device into the vascular lumen.

46. The method of claim 45, wherein the reentry device includes a penetrator, and wherein the penetrator is configured to pierce the intimal layer of the vascular wall before the distal end of the reentry device is advanced into the vascular lumen.

47. The method of claim 40, further comprising advancing the distal end of the reentry device into the vascular lumen if it is determined that the distal end of the reentry device is directed toward the vascular lumen.

48. The method of claim 40, further comprising withdrawing the distal end of the reentry device into the first intravascular device if it is determined that the distal end of the reentry device is directed away from the vascular lumen.

49. The method of claim 40, further comprising withdrawing one of a guidewire and the reentry device from a guidewire lumen of the first intravascular device and advancing the other of the guidewire and the reentry device into the guidewire lumen of the first intravascular device.

50. The method of claim 40, further including:
  positioning a second intravascular device in the vascular wall prior to positioning the distal portion of the first intravascular device in the vascular wall; and
  advancing a distal portion of the second intravascular device in the vascular wall beyond the occlusion.

51. The method of claim 50, further including advancing a guidewire through a lumen of the second intravascular device, and removing the second intravascular device from the vascular wall while leaving the guidewire in the vascular wall.

52. The method of claim 40, wherein the first intravascular device includes a first radiopaque marker and a second radiopaque marker, the first aperture being longitudinally offset from the second aperture with the first aperture located proximal the second aperture, the first radiopaque marker being located between the first aperture and the second aperture, the second radiopaque marker being located distal the second aperture.

53. The method of claim 40, further including a penetrator located at a distal tip of the distal end.

* * * * *

UNITED STATES PATENT AND TRADEMARK OFFICE
CERTIFICATE OF CORRECTION

PATENT NO.        : 8,202,246 B2                                    Page 1 of 1
APPLICATION NO.   : 12/320792
DATED             : June 19, 2012
INVENTOR(S)       : Chad J. Kugler et al.

It is certified that error appears in the above-identified patent and that said Letters Patent is hereby corrected as shown below:

Claim 30, Column 15, Line 21, "distal end tip" should read -- distal end --.

Claim 30, Column 15, Lines 23-24, "distal end tip" should read -- distal end --.

Claim 31, Column 15, Line 26, "distal end tip" should read -- distal end --.

Claim 31, Column 15, Line 27, "distal end tip" should read -- distal end --.

Claim 32, Column 15, Line 30, "distal end tip" should read -- distal end --.

Claim 32, Column 15, Line 31, "distal end tip" should read -- distal end --.

Claim 40, Column 16, Line 14, "first intravascular" should read -- first intravascular device --.

Signed and Sealed this
Thirtieth Day of October, 2012

David J. Kappos
*Director of the United States Patent and Trademark Office*